United States Patent
Roux et al.

(10) Patent No.: US 11,649,253 B2
(45) Date of Patent: May 16, 2023

(54) TERBIUM AND DYSPROSIUM COMPLEXES WITH OPTIMISED ANTENNA, USED AS LUMINESCENT MARKERS

(71) Applicants: ECOLE NORMALE SUPERIEURE DE LYON, Lyons (FR); CENTRE NATIONAL DE LA RECHERCHE SCIENTIFIQUE, Paris (FR); UNIVERSITE CLAUDE BERNARD LYON 1, Villeurbanne (FR)

(72) Inventors: Amandine Roux, Le Peage de Roussillon (FR); Anh-Thy Bui, Pessac (FR); Olivier Maury, Brindas (FR); Chantal Andraud, Genas (FR)

(73) Assignees: ECOLE NORMALE SUPERIEURE DE LYON, Lyons (FR); CENTRE NATIONAL DE LA RECHERCHE SCIENTIFIQUE, Paris (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 542 days.

(21) Appl. No.: 16/628,854

(22) PCT Filed: Jul. 5, 2018

(86) PCT No.: PCT/EP2018/068302
§ 371 (c)(1),
(2) Date: Jan. 6, 2020

(87) PCT Pub. No.: WO2019/008118
PCT Pub. Date: Jan. 10, 2019

(65) Prior Publication Data
US 2020/0223869 A1    Jul. 16, 2020

(30) Foreign Application Priority Data

Jul. 6, 2017    (FR) ................................ FR1756385

(51) Int. Cl.
*C01F 5/00* (2006.01)
*C07F 5/00* (2006.01)
*G01N 21/76* (2006.01)

(52) U.S. Cl.
CPC ............. *C07F 5/003* (2013.01); *G01N 21/76* (2013.01)

(58) Field of Classification Search
CPC ................................ C07F 5/003; G01N 21/76
(Continued)

(56) References Cited

U.S. PATENT DOCUMENTS

2008/0167443 A1 *    7/2008    Hovinen ............... C07F 9/6515
540/472

FOREIGN PATENT DOCUMENTS

| EP | 2734518 B1 | 4/2016 |
| EP | 2981590 B1 | 9/2019 |

(Continued)

OTHER PUBLICATIONS

Placide et al. "Two-photon multiplexing bio-imaging using a combination of Eu- and Tb-bioprobes" Dalton Trans., 2015, 44, 4918 (Year: 2015).*

(Continued)

*Primary Examiner* — Christine T Mui
*Assistant Examiner* — Emily R. Berkeley
(74) *Attorney, Agent, or Firm* — BCF LLP

(57) ABSTRACT

The present technology relates to luminescent lanthanide complexes comprising a chelating agent, formed of a macrocycle or ligand, complexing a lanthanide ion $Ln^{3+}$ selected from terbium and dysprosium, the chelating agent comprising at least one group of the structure (B) below; and a process for detecting a biomolecule using said lanthanide complex comprising coupling a luminescent lanthanide (Continued)

a       b       c       d complex of the present technology having a reactive group with said biomolecule.

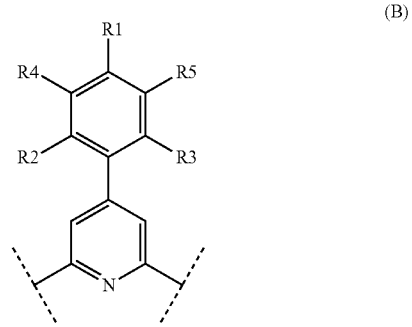

(B)

23 Claims, 2 Drawing Sheets

(58) Field of Classification Search
USPC .......................................................... 435/29
See application file for complete search history.

(56) References Cited

FOREIGN PATENT DOCUMENTS

| WO | 2005/058877 A1 | 6/2005 |
|----|----------------|--------|
| WO | 2013/026790 A9 | 2/2013 |
| WO | 2013/092992 A1 | 6/2013 |
| WO | 2014/147288 A1 | 9/2014 |

OTHER PUBLICATIONS

Alpha et al., "Energy Transfer Luminescence of Europium(III) and Terbium(III) Cryptates of Macrobicyclic Polypyridine Ligands", Angew. Chem. Int., Ed. Engl. 26(1987) No. 3, pp. 266-267.
Cao et al., "Substituent Effects on Oxidation-Induced Formation of Quinone Methides from Arylboronic Ester Precursors", Chem. Eur. J. 2013, 19, 9050-9058.
D'Aleo et al., "Design of Dipicolinic Acid Ligands for the Two-Photon Sensitized Luminescence of Europium Complexes with Optimized Cross-Sections", Inorg. Chem. 2008, 47, 10269-10279.
D'Aleo et al., "Efficient Sensitization of Europium, Ytterbium, and Neodymium Functionalized Tris-Dipicolinate Lanthanide Complexes through Tunable Charge-Transfer Excited States", Inorg. Chem. 2008, 47, 10258-10268.
D'Aleo et al., "Charge transfer excited states sensitization of lanthanide emitting from the visible to the near-infra-red", Coordination Chemistry Reviews 256 (2012), 1604-1620.
Eliseeva et al., "Lanthanide luminescence for functional materials and bio-sciences", Chem. Soc. Rev., 2010, 39(1), 187-227.
Green et al., "Protective Groups in Organic Synthesis",Third Edition,1999, John Wiley & Sons, Inc., ISBN 0471160199.
Hermanson, "Bioconjugate Techniques", Second Edition, 2008, Academic Press, ISBN 9780123705013.
Kocienski, "Protecting Groups", Third Edition, 2005, Georg Thieme Verlag, ISBN 3131356030.
Mohandessi et al., "Cell-Penetrating Peptides as Delivery Vehicles for a Protein-Targeted Terbium Complex", Chem. Eur. J., 2012, 18, 10825-10829.
Montgomery et al., "Cell-Penetrating Metal Complex Optical Probes: Targeted and Responsive Systems Based on Lanthanide Luminescence", Accounts of Chemiclal Research, 2009, 42(7), 925-937.
Moore et al., "From Antenna to Assay: Lessons Learned in Lanthanide Luminescence", Accounts of Chemical Research, 2009, 42(4), 542-552.
Moore et al., "From Antenna to Assay: Lessons Learned in Lanthanide Luminescence", NIH Public Access, Acc. Chem. Res., Apr. 2009, 42(4), 542-552.
Placide et al., "Two-photon multiplexing bio-imaging using a combination of Eu- and Tb-bioprobes", Dalton Trans., 2015, 44, 4918-4924.
Soulie et al., "Comparative Analysis of Conjugated Alkynyl Chromophore-Triazacyclononane Ligands for Sensitized Emission of Europium and Terbium", Chem. Eur. J., 2014, 20, 8636-8646.
Walton et al., "Very bright europium complexes that stain cellular mitochondria", Chem. Cmmun., 2013, 49, 1600-1602.
Xu et al., "Octadentate Cages of Tb(III) 2-Hydroxyisophthalamides: A New Standard for Luminescent Lanthanide Labels", J. Am. Chem. Soc., 2011, 133, 19900-19910.
Zou et al., "Cytoplasmic Delivery and Selective, Multicomponent Labeling with Oligoarginine-Linked Protein Tags", Bioconjugate Chem., 2015, 26, 460-465.

* cited by examiner

TERBIUM AND DYSPROSIUM COMPLEXES WITH OPTIMISED ANTENNA, USED AS LUMINESCENT MARKERS

CROSS-REFERENCE TO RELATED APPLICATIONS

This application is a national phase filing under 35 U.S.C. § 371 of International Application No. PCT/EP2018/068302 filed on Jul. 5, 2018, which claims benefit of priority from French Patent Application No. 1756385 filed Jul. 6, 2017, the contents of which are hereby incorporated by reference in their entirety.

The invention relates to the technical field of lanthanide complexes. In particular, the invention relates to lanthanide complexes comprising a chelating agent, formed of a macrocycle or ligand, and complexing a lanthanide ion, corresponding chelating agents, as well as a process for detecting a biomolecule using said lanthanide complex.

Some luminescent lanthanide complexes have remarkable spectroscopic properties (thin emission bands characteristic of a given metal and with a long lifetime) and are therefore compounds with very high potential for biological imaging applications (S. V. Eliseeva, J.-C. G. Bünzli, *Chem. Soc. Rev.* 2010, 39, 189). These luminescent compounds can be used alone for imaging applications by single or biphotonic fluorescence microscopy, or in conjunction with a suitable fluorophore to perform FRET (Förster/Fluorescence Resonant Energy Transfer) experiments. In the latter case, lanthanide complexes are generally in the form of a complex conjugated to a biomolecule. Both techniques can eventually be solved in time thanks to the long lifetime of lanthanides, which is an important advantage in improving detection, by eliminating the need for short-lived parasitic fluorescence signals (C. P. Montgomery B. S. Murray, E. J. New, R. Pal, D. Parker, *Acc. Chem. Res.* 2009, 42, 925; E. G. Moore, A. P. S. Samuel, K. N. Raymond, *Acc. Chem. Res.* 2009, 42, 542).

Such luminescent lanthanide compounds have already been described in the literature, and some are even marketed by Cisbio Bioassays, PerkinElmer or Invitrogen. In recent years, functionalized lanthanide complexes have been developed to optimize their spectroscopic properties, shift their absorption towards the visible, optimize their biphotonic absorption, and improve their solubility in aqueous media.

In particular, document WO 2005/058877 describes lanthanide complexes based on 1,4,7-triazacyclonane (TACN) rings with three nitrogen atoms substituted by chromophores consisting of a pyridine derivative optionally substituted by a reactive group, in order to facilitate conjugation with biomolecules. The objective is to provide highly fluorescent, stable and easily graftable complexes to a biomolecule. In particular, this document describes a TACN terbium complex in which the three nitrogen atoms are substituted by a 2-carboxylate-4-(2,4,6-trimethoxyphenyl)-pyridine group (compound 22) but does not indicate the brightness measured for this compound.

In addition, some of the inventors have previously described terbium complexes based on 1,4,7-triazacyclononane (TACN) rings in which three nitrogen atoms are substituted by chromophores composed of a pyridine derivative (V. Placide, A. T. Bui, A. Grichine, A. Duperray, D. Pitrat, C. Andraud, O. Maury, *Dalton Trans.* 2015, 44, 4918). In particular, this document describes a TACN terbium complex in which the three nitrogen atoms are substituted by a 2-carboxylate-4-(4-methoxyphenyl)-pyridine group, which has intense absorption but low quantum efficiency and brightness.

There is therefore a need for lanthanide complexes with good brightness, particularly when excited in the spectral range of interest from 330 nm to 350 nm, and more particularly around 337 nm (wavelength corresponding to laser sources often used in bioassays). The structure of the complexes according to the invention makes it possible to achieve chemical variations that advantageously obtain good solubility and stability in biological environments and allow easy grafting onto a biomolecule.

Brightness is defined as the product of absorption at the wavelength of interest and quantum emission efficiency and corresponds to the amount of light actually available for the imaging and/or FRET experiment. Optimal brightness optimizes the signal-to-noise ratio, thus increasing the sensitivity of detection and/or reducing the amount of chromophore used.

The Inventors propose novel lanthanide complexes comprising a chelating agent, formed of a macrocycle or ligand, complexing a lanthanide ion $Ln^{3+}$ selected from terbium and dysprosium, the chelating agent comprising at least one group of the following structure (B):

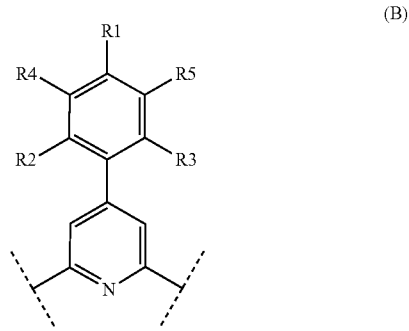

(B)

wherein:
- —R1 represents a hydrogen, a group —R6, or an electron-donating group -E1,
- —R2 represents a hydrogen, a group —R7, or an electron-donating group -E2,
- —R3 represents a hydrogen, a group —R8, or an electron-donating group -E3,
- —R4 and —R5, identical or different, independently represent a hydrogen or a group —R9 or —OR9,
- -E1, -E2 and -E3 are independently selected from the groups —OR10, —SR10, —NH(CO)R10, —NH(CO)NR10R'10, —NH(CS)NR10R'10 and —NH(CS)NHR10,
- —R6, —R7, —R8, —R9, —R10 and R'10 identical or different, independently represent a (C1-C6) alkyl group, optionally substituted by a group —X1 or a group —Y,
- —X1 is a reactive group,
- —Y is a water-solubilizing group, it being understood that:
- at least one of the substituents —R2 and —R3 is not hydrogen,
- only one of the groups —R1, —R2 and —R3 represents an electron-donating group,
- said chelating agent comprises at most one reactive group.

The complexes of the invention are luminescent. Luminescence corresponds to an emission of light following an energy supply, in particular a supply of light. This energy supply causes atoms or molecules to pass into an "excited" state at an energy higher than that which they possess in their normal "fundamental" state. It is when they return to their fundamental state that they can emit light. In general, lanthanide complexes are sensitized by antenna effect and the nature of the organic antenna controls light absorption and optimizes lanthanide luminescence (S. V. Eliseeva, J.-C. Bünzli, *Chem. Soc. Rev.* 2010, 39, 189).

The complexes according to the invention have the advantage of having a high brilliance, in particular due to a very high quantum yield, in particular in hydrophilic medium and in particular in aqueous medium. Without wishing to be bound by any theory, the inventors believe that the improvement of quantum efficiency, and the optimization of brightness, of the complexes of the invention is due to the combination of the electronic and steric effects of the antennas (i.e. the groups (B)). The presence of a single electron-donating group significantly improves quantum efficiency. Thus, surprisingly, particularly in relation to document WO 2005/058877, the inventors observed a drastic drop in quantum efficiency when several electron-donating groups are present, compared to the same complex with only one electron-donating group. In addition, it appears that the introduction of groups in position R2 and/or R3 avoids the internal rotation of the antenna around the pyridine-phenyl bond, which contributes to an increase in non-radiative de-excitations and leads to a decrease in quantum efficiency. Thus, the steric clutter of the groups —R2 and/or —R3, both of which are not hydrogen in the complexes of the invention, would block this rotation and would therefore be important for the final brightness of the complex.

In addition, the complexes according to the invention may be provided with a reactive group, which may be covalently conjugated to a molecule of interest, such as a biomolecule. The complexes according to the invention can also be provided with one or more water-solubilizing groups, which thus improves their solubility in a hydrophilic medium, and in particular in an aqueous medium.

In the context of the invention, "alkyl" refers to a saturated hydrocarbon chain, which may be linear or branched. Examples of alkyl groups containing 1 to 6 carbon atoms include methyl, ethyl, n-propyl, iso-propyl, n-butyl, iso-butyl, tert-butyl, sec-butyl, n-pentyl, iso-pentyl, tert-pentyl, neo-pentyl, dry-pentyl, and n-hexyl groups.

In a preferred manner in the context of the invention, the lanthanide Ln is terbium. Terbium complexes are indeed very bright.

Advantageously, lanthanide complexes, according to the invention, include a reactive group, noted —X, —X1 or —X2, allowing its coupling by covalent binding to a biomolecule. According to the very definition of the chelating agent forming the complex, only one reactive group may be present.

"Reactive group" means a group comprising a function that allows covalent grafting on a reactive function and present on a biomolecule (amine, alcohol, thiol, carboxylic acid, unsaturation, etc.). The different functions allowing such bio-conjugation are well known to the skilled person and are described, for example, in *Bioconjugate Techniques*, G. T. Hermanson, 1996, 137-166.

"Biomolecules" refers to molecules of biological interest that may be advantageously labelled with a luminescent complex. Examples of biomolecules include proteins, peptides, antibodies, antigens, DNA strands, biotin and streptavidin. Proteins are the biomolecules that will most often be linked to the complexes of the invention.

In the context of the invention, the reactive group may be selected from —COOH, —NH$_2$, an acrylamide, activated amine, activated ester, aldehyde, alkyl halide, anhydride, aniline, azide, aziridine, carboxylic acid, diazoalkane, haloacetamide, halotriazine, hydrazine, imido ester, isocyanate, isothiocyanate, maleimide, sulfonyl halide, thiol, ketone, acid halide, hydroxysuccinimidyl ester, succinimidyl ester, hydroxysulfosuccinimidyl ester, azidonitrophenyl, azidophenyl, 3-(2-pyridyl dithio)-propionamide, glyoxal, triazine, acetylenic group, and the groups of formula:

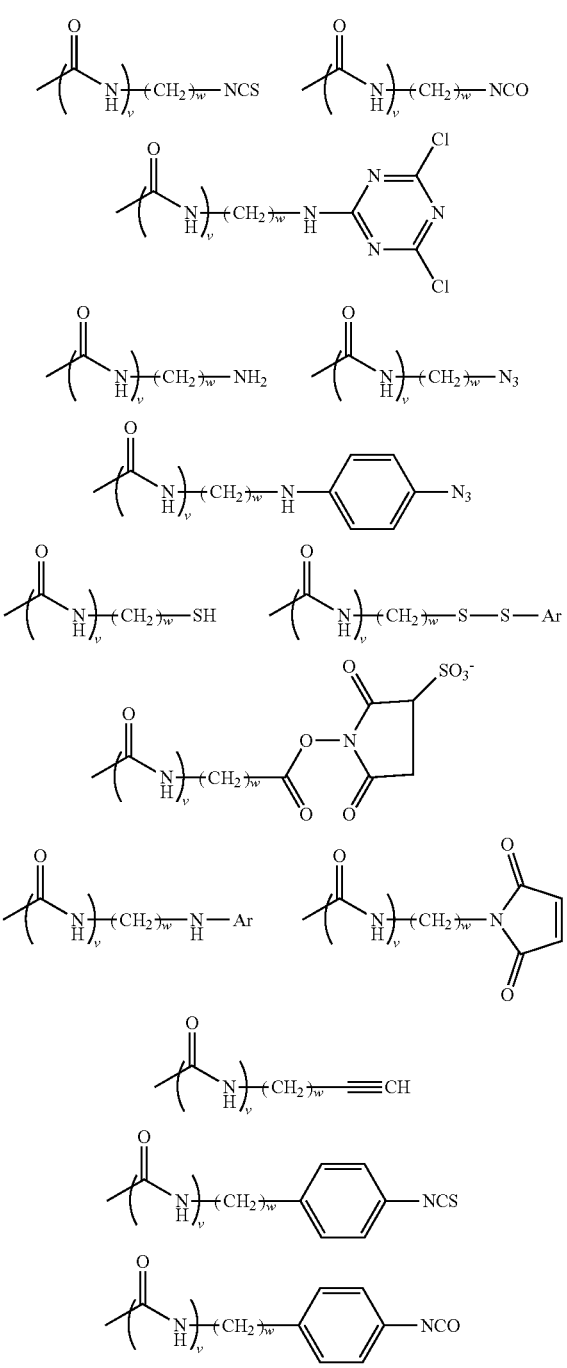

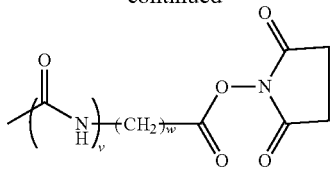

wherein w is an integer belonging to the range of 0 to 8 and v is 0 or 1, and Ar is a saturated or unsaturated 5- or 6-membered heterocycle, comprising 1 to 3 heteroatoms, optionally substituted by a halogen atom; the reactive groups selected from —COOH, —NH$_2$, succinimidyl esters, haloacetamides, azides, hydrazines, isocyanates and maleimides being preferred.

Preferably, the complexes according to the invention include at least one and at most 15 water-solubilizing groups, labelled —Y, and advantageously at least 2, and preferably from 2 to 9 water-solubilizing groups, in particular from 2 to 5, and preferably 2 or 3.

"Water-solubilizing group" means a group that includes a function that improves solubility in a hydrophilic environment.

In the context of the invention, the water-solubilizing group(s) —Y may be selected from the groups —SO$_3^-$, —COO$^-$, sulfobetaine and —O—[(CH$_2$)$_2$—O]$_m$—CH$_3$, m being an integer from 1 to 10, preferably m=3. According to a preferred embodiment, the water-solubilizing group(s) are selected from groups —O—[(CH$_2$)$_2$—O]$_m$—CH$_3$, m being an integer from 1 to 10, preferably m=3.

"Sulfobetaine" refers to a betaine group with a —SO$_3$ function as a negative charge-bearing function. A betaine group is defined as a zwitterionic group in which the positively charged atom does not carry a hydrogen atom and is not adjacent to the negatively charged atom. In the context of the invention, sulfobetaine refers, for example, to zwitterionic groups combining an ammonium cation, or aromatic iminium, generally pyridinium, imidazollium, and an anionic group of the sulfonate type. The cation and anion are separated by at least one CH$_2$ chain, and preferably by a bivalent alkyl chain (also called alkylene) containing from 1 to 4, or even from 1 to 6, carbon atoms. Examples of sulfobetaine groups include the groups of formula:

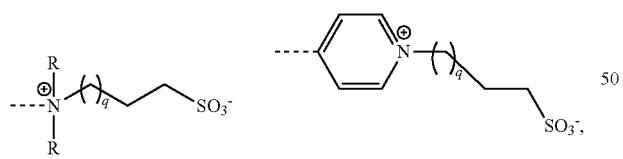

with R which represents an alkyl group of 1 to 6 carbon atoms, and preferably a methyl or ethyl, and q which is equal to 1, 2, 3, 4, 5 or 6, and preferably which is equal to 1 or 2. The group —N(CH$_3$)$_2^+$—(CH$_2$)$_3$—SO$_3^-$ is preferred.

When the complexes according to the invention include one or more water-solubilizing groups, these may be on any substituent of the phenyl group of the structural group (B), i.e. on —R1, —R2, —R3, —R4 and/or —R5, or plus precisely on —R6, —R7, —R8, —R9, —R10 and/or —R'10. Preferably, the water-solubilizing groups are in ortho and/or para position with respect to the pyridinyl group of the structural group (B), i.e. on —R6, —R7, —R8, —R10 and/or —R'10, and preferably para.

According to a first embodiment, the lanthanide complexes according to the invention are selected from the lanthanide complexes of formula (I):

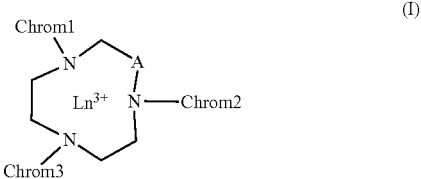

wherein:
Ln is a lanthanide selected from Tb and Dy,
-A- represents —CH$_2$— or —CH(L$_A$-X2)-,
-L$_A$- is a covalent bond, or a linear or branched (C1-C20) alkylene group, optionally containing one or more double or triple bonds, and optionally substituted by one to three groups —SO$_3$H, or -L$_A$- is a (C5-C8) cycloalkylene group or a (C6-C14) arylene group,
—X2 is a reactive group,
-Chrom1, -Chrom2 and -Chrom3 are identical or different and independently selected from the groups of formula (B1):

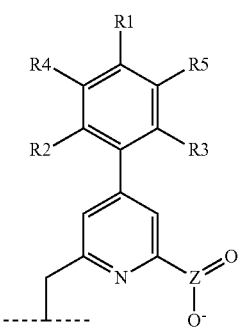

—R1, —R2, —R3, —R4, and —R5 are as defined for the group of formula (B),
—Z— represents —C— or —P(R$_Z$)—, and
—R$_Z$ represents a phenyl, benzyl, methyl, ethyl, propyl, n-butyl, sec-butyl, iso-butyl or tert-butyl group, and preferably a phenyl or methyl group,
it being understood that if -A- is —CH(L$_A$-X2)-, then none of groups -Chrom1, -Chrom2 and -Chrom3 of formula (B1) has group —X1.
Preferably, in the complexes of formula (I), -A- represents —CH$_2$—, and/or —Z— represents —C—, and/or —R4 represents a hydrogen, and/or —R5 represents a hydrogen in -Chrom1, -Chrom2 and -Chrom3.

Preferably, in the complexes of formula (I), —R4 and —R5 represent hydrogens in -Chrom1, -Chrom2 and -Chrom3.

According to a preferred embodiment, the lanthanide complexes (I) are such that -A-represents —CH$_2$—, —Z— represents —C— and —R4=—R5=H in -Chrom1, -Chrom2 and -Chrom3.

According to an embodiment, -Chrom1, -Chrom2 and -Chrom3 are identical in the complexes (I). These complexes will be named (Ia). These complexes (Ia) then have the advantage of being easier to synthesize.

According to an embodiment, in the complexes (Ia), —R1 represents an electron-donating group -E1 as defined for the groups of formula (B), particularly selected from the groups —OR10 and —NH(CO)R10, —R10 being as defined for the groups of formula (B). Preferably, —R1 represents a group —OR10, and in particular —OMe or —OPEG, in the complexes (Ia).

According to an embodiment, in the complexes (Ia), —R2 is a group —R7 as defined for the groups of formula (B). Preferably, in the complexes (Ia), —R2 represents -Me.

According to an embodiment, in the complexes (Ia), —R3 is advantageously a hydrogen or a group —R8 as defined for the groups of formula (B), preferentially -Me. Preferably, —R3 is a hydrogen in the complexes (Ia).

According to a particular embodiment of the complexes of formula (I), -Chrom1, -Chrom2 and -Chrom3 are identical and such that —R1 represents a group -E1, particularly selected from the groups —OR10 and —NH(CO)R10, —R2 is a group —R7, and in particular -Me, and —R3 is a hydrogen or a group —R8, preferably -Me, -E1, —R7, —R8 and —R10 being as defined for the groups of formula (B).

According to a particular embodiment of the complexes of formula (I), -Chrom1, -Chrom2 and -Chrom3 are identical and such that —R1 represents a group —OR10, —R2 is a group —R7, and in particular -Me, and —R3 is a hydrogen, —R7 and —R10 being as defined for the groups of formula (B).

According to another embodiment, -Chrom1 and -Chrom2 are identical and -Chrom3 is different from -Chrom1 and from -Chrom2. These complexes will be named (Ib).

According to a particular embodiment, the lanthanide complexes (Ib) are such that:

-A- represents —CH$_2$—,

-Chrom1 and -Chrom2 are identical and are of structure (B2):

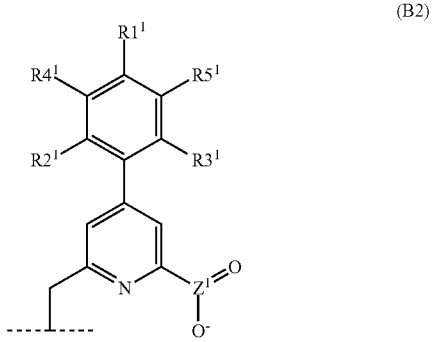

(B2)

with —R1$^1$, —R2$^1$, —R3$^1$, —R4$^1$, —R5$^1$ and —Z$^1$— as defined respectively for R1, —R2, —R3, —R4, —R5 and —Z— in the groups of formula (B), it being understood that Chrom1 and -Chrom2 do not have a reactive group, and -Chrom3 is different from -Chrom1 and from -Chrom2 and is of structure (B3):

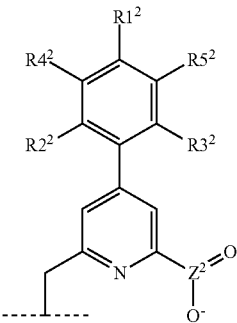

(B3)

with —R1$^2$, —R2$^2$, —R3$^2$, —R4$^2$, —R5$^2$ and —Z$^2$— as defined respectively for R1, —R2, —R3, —R4, —R5 and —Z— in the groups of formula (B), it being understood that -Chrom3 has a reactive group.

According to an embodiment, in the complexes (Ib), —R1$^1$ represents a group —OR10$^1$, preferably —OMe or —OPEG, or a group —NH(CO)R10$^1$, —R10$^1$ being as defined for —R10 in the group of formula (B). Preferably, in the complexes (Ib), —R1$^1$ represents a group —OR10$^1$, preferably —OMe or —OPEG, —R10$^1$ being as defined for —R10 in the group of formula (B).

In the complexes (Ib), —R1$^2$ represents advantageously a group —NH(CO)R10$^2$, or, preferably —OR10$^2$, with R10$^2$ which is a group —O(C1-C6) alkyl substituted by a group —X1.

In the complexes (Ib), —R2$^1$ and —R2$^2$, identical or different, represent advantageously a group —R7 as defined for the groups of formula (B). Preferably, in the complexes (Ib), —R2$^1$ and —R2$^2$ are identical and represent, preferentially, -Me.

In the complexes (Ib), —R3$^1$ and —R3$^2$, identical or different, represent a hydrogen or a group —R8 as defined for the groups of formula (B). Preferably, in the complexes (Ib), R3$^1$ and —R3$^2$ are identical and represent -Me or, preferentially, a hydrogen.

According to a particular embodiment, in the complexes (Ib), —R1$^1$ represents a group —OR10$^1$, preferably —OMe or —OPEG, and —R1$^2$ represents —OR10$^2$, preferably a group —O(C1-C6) alkyl substituted by a group —X1, —R10$^1$ and —R10$^2$ being as defined for —R10 in the groups of formula (B).

According to a particular embodiment, in the complexes (Ib), —R2$^1$ and —R2$^2$ are identical and represent a group —R7, and —R3$^1$ and —R3$^2$ are identical and represent a hydrogen or a group —R8 such as -Me, the groups —R7 and —R8 being as defined for the groups of formula (B).

According to a particular embodiment, in the complexes (Ib), —R2$^1$ and —R2$^2$ are identical and represent a group —R7 as defined for the groups of formula (B), and preferentially -Me, and —R3$^1$ and —R3$^2$ are identical and represent a hydrogen.

According to a particular embodiment of the complexes of formula (Ib), —R1$^1$ represent a group —OR10$^1$, preferably —OMe or —OPEG, —R1$^2$ represents a group —OR10$^2$, preferably a group —O(C1-C6) alkyl substituted by a group —X1, —R2$^1$ and —R2$^2$ are identical and represent a group —R7, preferably -Me and —R3$^1$ and —R3$^2$ are identical and represent a hydrogen, —R1$^1$, —R1$^2$, —R2$^1$, —R2$^2$, R3$^1$, —R3$^2$ and —R10$^1$ as defined respectively for —R1, —R1, —R2, —R2, R3, —R3 and —R10 for the groups of formula (B).

Advantageously, in the groups of formula (B), one of groups —R2 or —R3 represents a hydrogen. Similarly, in the groups of formula (B1), one of groups —R2$^1$ or —R3$^1$ represents advantageously a hydrogen. Similarly, in the groups of formula (B2), one of groups —R2$^2$ or —R3$^2$ represents advantageously a hydrogen.

In particular, -Chrom1, -Chrom2 and -Chrom3 are identical or different, and independently selected from the groups of the following formula (B4):

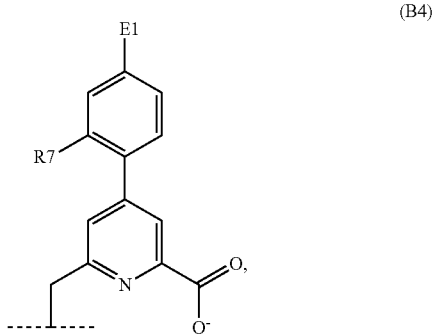

(B4)

with —R7 and -E1 as defined for the groups of formula (B), —R7 representing preferably -Me, and -E1 representing preferably a group —OR10 or —NH(CO)R10 optionally substituted by a group —Y or a group —X1, R10 being as defined for the groups of formula (B).

According to a particular embodiment, the lanthanide complexes (I) according to the invention are such that:
- —R1$^1$ is a group —O(C1-C6) alkyl substituted by a group —Y,
- —R1$^2$ is a group —O(C1-C6) alkyl substituted by a group —X1,
- —R2$^1$ and —R2$^2$, identical or different, represent a group —R7 as defined for the groups of structure (B), and are preferably identical and represent, preferentially, a (C1-C6) alkyl group, particularly -Me, and
- —R3$^1$, —R3$^2$, —R4$^1$, —R4$^2$, —R5$^1$ and —R5$^2$ are hydrogens.

According to this particular embodiment, the lanthanide complexes are of formula (Ib'):

(Ib')

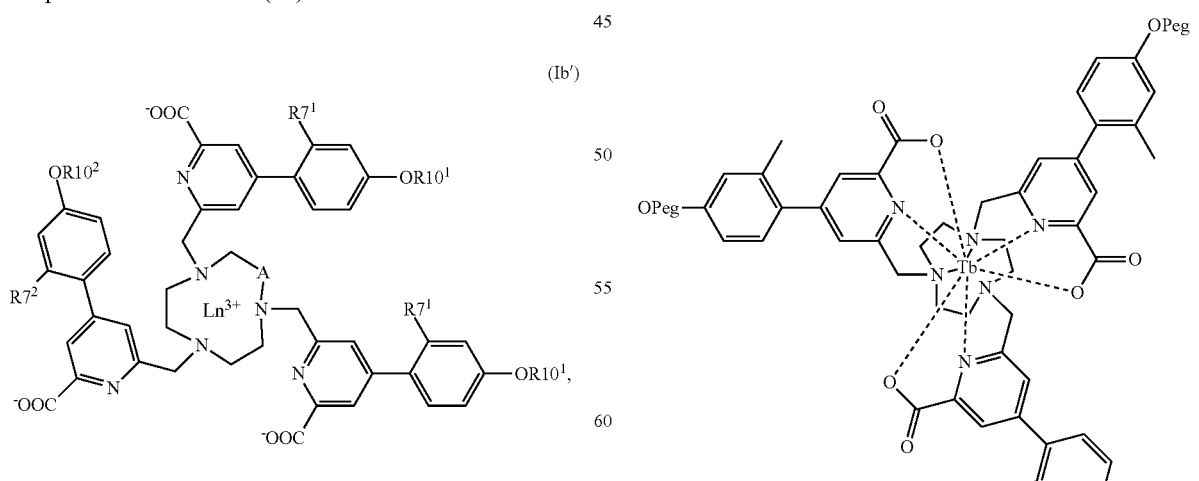

with A as defined for the complexes (I), —R7$^1$ and —R7$^2$ as defined for —R7 for the groups of formula (B), —R10$^1$ representing a (C1-C6) alkyl group substituted by a group —X1 and —R10$^2$ representing a (C1-C6) alkyl group substituted by a group —Y.

According to a particular embodiment of the invention, the lanthanide complexes (I) are selected from the following complexes:

Ia.1

Ia.2

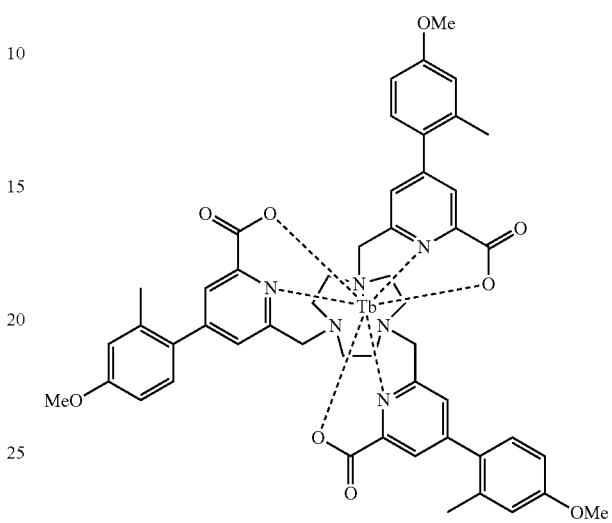

Ia.3

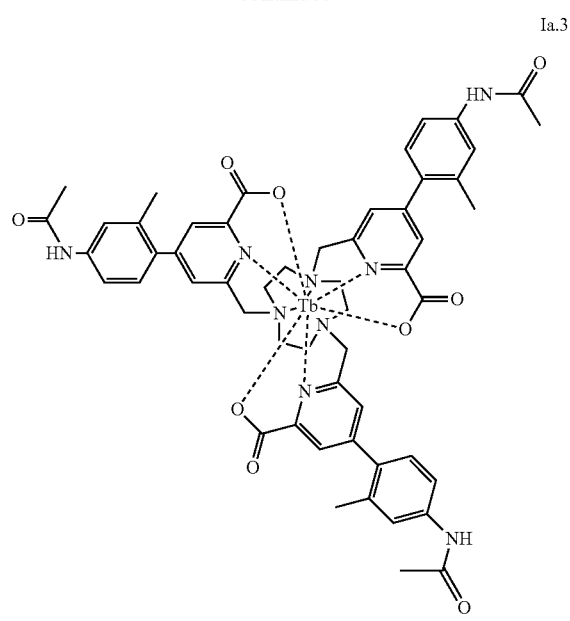

Ia.4

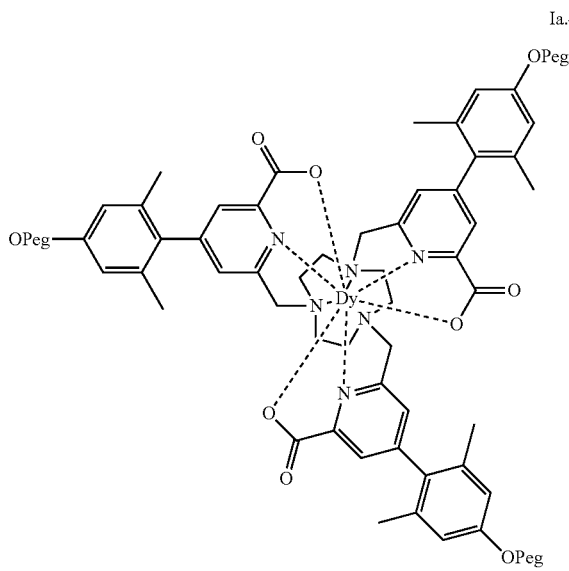

Ia.5

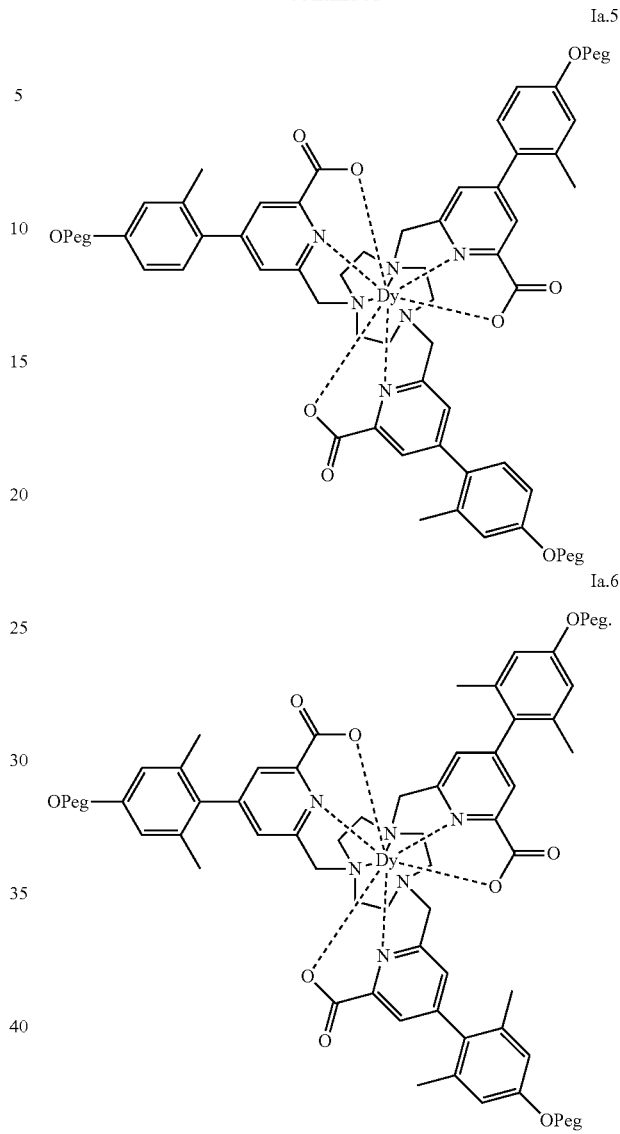

Ia.6

A particularly preferred lanthanide complex is the complex (Ia.2).

According to a second embodiment, the lanthanide complexes according to the invention are selected from the lanthanide complexes of formula (II):

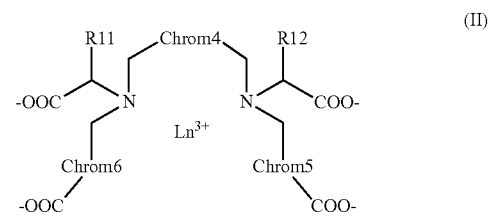

(II)

wherein:

Ln is a lanthanide selected from Tb and Dy,

—R11 and —R12, identical or different, are independently selected from —X1, —Y, a hydrogen atom or a (C1-C6) alkyl group, -Chrom4-, -Chrom5-, and -Chrom6-, identical or different, independently represent a group of formula (B), as defined in the context of the invention.

Preferably, —R4 and/or —R5 represents a hydrogen in -Chrom4-, -Chrom5- and -Chrom6-. Preferably, —R4 and —R5 represent hydrogens in -Chrom4-, -Chrom5- and -Chrom6-.

According to an embodiment, -Chrom4-, -Chrom5- and -Chrom6- are identical. These complexes will be named (IIa).

In the complexes (IIa), —R1 represents advantageously an electron-donating group -E1 as defined for the groups of formula (B), particularly selected from the groups —OR10 and —NH(CO)R10, —R10 being as defined for the groups of formula (B). Preferably, —R1 represents a group —OR10, and in particular —OMe or —OPEG in the complexes (IIa).

In the complexes (IIa), —R2 is advantageously a group —R7 as defined for the groups of formula (B). Preferably, —R2 represents -Me in the complexes (IIa).

In the complexes (IIa), —R3 is advantageously a hydrogen or a group —R8 as defined for the groups of formula (B), preferentially -Me. Preferably, —R3 is a hydrogen in the complexes (IIa).

According to another embodiment, the lanthanide complexes (II), named (IIb), are such that:
-Chrom5- and -Chrom6- are identical and are of structure (B10):

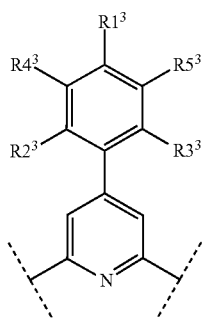

(B10)

with —R1³, —R2³, —R3³, —R4³, and —R5³ as defined respectively for —R1, —R2, —R3, —R4, and —R5 in the groups of structure (B), it being understood that -Chrom5- and -Chrom6- do not have a reactive group, and
-Chrom4- is different from -Chrom5- and from -Chrom6- and is of structure (B11):

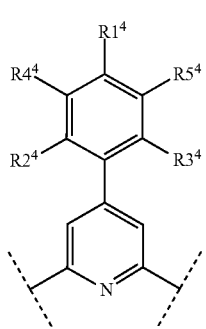

(B11)

with —R1⁴, —R2⁴, —R3⁴, —R4⁴ and —R5⁴ as defined respectively for —R1, —R2, —R3, —R4 and —R5 in the groups of structure (B), it being understood that -Chrom4- has a reactive group —X1.

According to another embodiment, the lanthanide complexes (II), named (IIc) are such that:
-Chrom4- and -Chrom6- are identical and are of structure (B12):

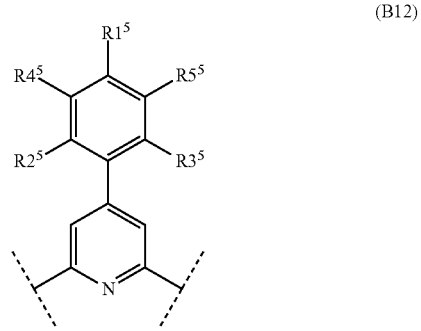

(B12)

with —R1⁵, —R2⁵, —R3⁵, —R4⁵ and —R5⁵ as defined respectively for —R1, —R2, —R3, —R4 and —R5 in the groups of formula (B), it being understood that -Chrom4- and -Chrom6- do not have a reactive group, and
-Chrom5- is different from -Chrom4- and from -Chrom6- and is of structure (B13):

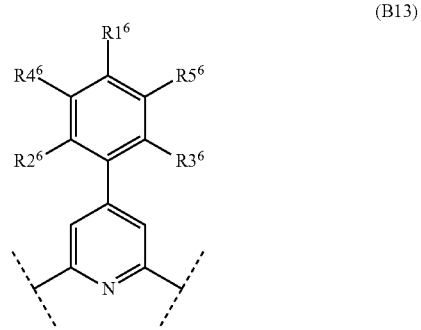

(B13)

with —R1⁶, —R2⁶, —R3⁶, —R4⁶ and —R5⁶ as defined respectively for —R1, —R2, —R3, —R4 and —R5 in the groups of formula (B), it being understood that -Chrom5- has a reactive group —X1.

Advantageously, in the complexes (IIb) and (IIc), —R1³ and —R1⁵, when present, are the groups —O(C1-C6) alkyl or —NH(CO)(C1-C6) alkyl optionally substituted by a group —Y. Preferably in the complexes (IIb) and (IIc), —R1³ and —R1⁵ are the groups —O(C1-C6) alkyl optionally substituted by a group —Y, and in particular —OMe or —OPEG.

Advantageously in the complexes (IIb) and (IIc), —R1⁴ and —R1⁶, when present, represent a group —O(C1-C6) alkyl or NH(CO)(C1-C6) alkyl substituted by a group —X1. Preferably in the complexes (IIb) and (IIc), —R1⁴ and —R1⁶ are the groups —O(C1-C6) alkyl optionally substituted by a group —X1.

In the complexes (IIb) and (IIc), R2³, —R2⁴, —R2⁵ and —R2⁶, when present, may be identical or different, and represent a group —R7 as defined for the groups of formula (B).

Preferably in the complexes (IIb) and (IIc), R2³, —R2⁴, —R2⁵ and —R2⁶, when present, are identical and represent, preferentially -Me.

In the complexes (IIb) and (IIc), R2³, —R2⁴, —R2⁵, and —R2⁶, when present, may be identical or different and represent a hydrogen or a group —R8 as defined for the groups of formula (B), preferentially -Me. Preferably, R2³, —R2⁴, —R2⁵, —R2⁶, when present, are identical and represent, preferentially a hydrogen.

In the complexes (IIb) and (IIc), R3³, —R3⁴, —R3⁵ and —R3⁶, when present, may be identical or different and represent a hydrogen or a group —R8 as defined for the groups of formula (B), preferentially -Me. Preferably, R3³, —R3⁴, —R3⁵ and —R3⁶, when present, are identical and represent a hydrogen.

Preferably in the complexes (IIb) and (IIc), —R3³, —R3⁴, —R3⁵ and —R3⁶, when present, are identical and represent advantageously hydrogens, and —R2³, —R2⁴, —R2⁵ and —R2⁶, when present, are identical and represent each a group —R7, as defined for the groups of formula (B), preferably -Me.

In particular, Chrom4-, -Chrom5- and -Chrom6- are identical or different, and independently selected from the groups of the following formula (B14):

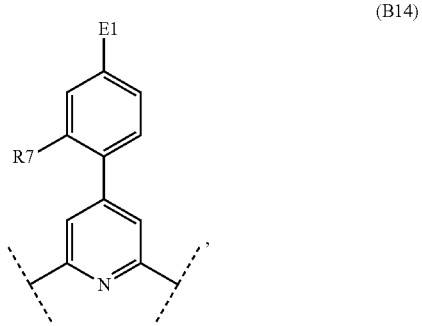

with —R7 and -E1 as defined for the groups of formula (B), and —R7 representing preferably -Me and -E1 representing preferably a group —OR10 or —NCO(NR10) optionally substituted by a group —Y or a group —X1, R10 being as defined for the groups of formula (B).

According to a particular embodiment of the invention, the lanthanide complexes (IIb) are such that:
—R1³ is a group —O(C1-C6) alkyl optionally substituted by a group —Y,
—R1⁴ is a group —O(C1-C6) alkyl substituted by a group —X1,
—R2³ and —R2⁴ are identical or different, preferably identical, and represent a group —R7, and in particular a (C1-C6) alkyl group, and
—R3³, R3⁴, —R4³, —R4⁴, —R5³ and —R5⁴ are hydrogens.

According to a particular embodiment of the invention, the lanthanide complexes (IIc) are such that:
—R1⁵ is a group —O(C1-C6) alkyl optionally substituted by a group —Y,
—R1⁶ is a group —O(C1-C6) alkyl substituted by a group —X1,
—R2⁵ and —R2⁶ are identical or different, preferably identical, and represent a group —R7, and in particular a (C1-C6) alkyl group, and
—R3⁵, R3⁶, —R4⁵, —R4⁶, —R5⁵ and —R5⁶ are hydrogens.

The invention also relates to chelating agents corresponding to the lanthanide compounds defined in the context of the invention, regardless of the variant embodiment described. The invention also relates to such chelating macrocycles in their protected form according to formula (III) and to such chelating ligands in their protected form according to formula (IV).

The invention also relates to chelating agents of formula (III):

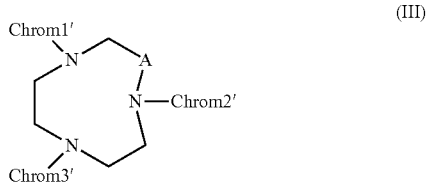

with -Chrom1', -Chrom2', and -Chrom3', identical or different, and independently selected from the groups of formula (B5):

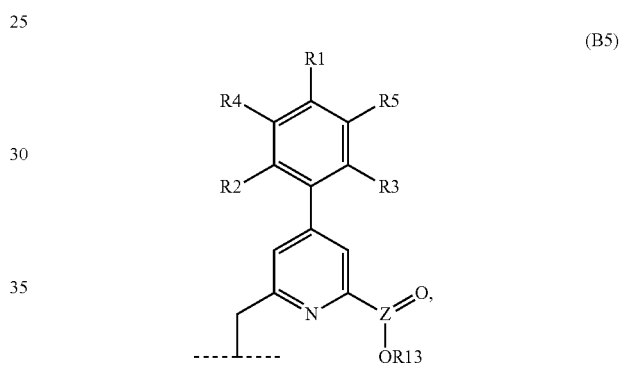

with R1, R2, R3, R4 and R5 as defined for the lanthanide complexes (I), and —R13 an acid-protecting group (i.e. —Z(O)OH), such as an alkyl, and particularly a methyl, or in the form of a salt.

The invention also relates to the chelating agents of formula (IV):

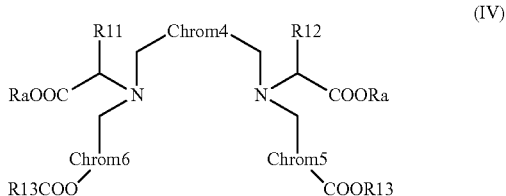

with -Chrom4-, -Chrom5- and -Chrom6- as defined for the lanthanide complexes of formula (II), and —R13 an acid-protecting group, such as an alkyl, and particularly a methyl, or in the form of a salt.

The preparation of complexes (I) and (II) according to the invention uses classical techniques and reactions known to the skilled person. In particular, they can be obtained using procedures similar to those described in the examples.

Complexing reactions are generally carried out with a salt of the desired lanthanide, such as chloride, nitrate or triflate, in a dissociating solvent, such as an alcohol such as methanol, THF or acetonitrile, or in a solvent mixture, usually in the presence of a carbonate, at a temperature between 25 and 80° C., for a period ranging from 30 minutes to several hours.

Compounds (III) and (IV) are relatively easy and conventional to access and can be obtained at a reasonable cost of preparation. The reagents are commercially available or easily accessible.

The functional groups possibly present in the compounds of formula (III) and (IV), and in the reaction intermediates, may be protected during synthesis, either in permanent or temporary form, by protecting groups which ensure a unique synthesis of the expected compounds.

Protection and deprotection reactions are carried out according to techniques well known to the skilled person. Temporary protecting group refers to protecting groups such as those described in *Protective Groups in Organic Synthesis*, Greene T. W. and Wuts P. G. M., ed. John Wiley & Sons, 2006, and in *Protecting Groups*, Kocienski P. J. 1994, Georg Thieme Verlag.

According to formula (I), the family of lanthanide complexes resulting from the coordination of a macrocyclic ligand of formula (III) after deprotection and release of the acid functions —Z(O)OH (dialkyl or diaryl phosphinic acid when —Z═—P(Rz)- or carboxylic acid when —Z═ C—) is described.

According to a first embodiment, -Chrom1', -Chrom2', and -Chrom3' are identical.

According to this embodiment, the chelating agent of formula (II) can be obtained by alkylation of a TACN.3HCl ring with an intermediate of formula (B6):

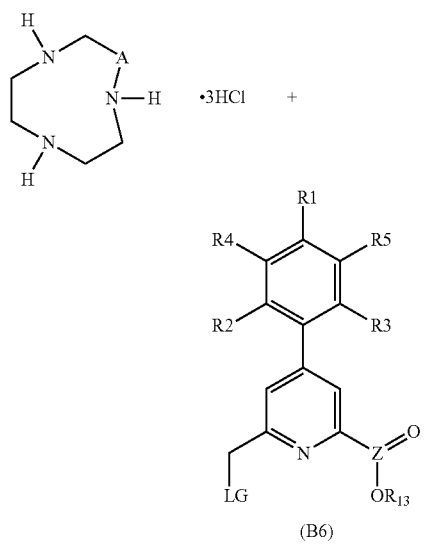

with -A-, —R1, —R2, —R3, —R4, —R5 and —R13 as defined for the chelating agents (III), and -LG representing a leaving group.

"Leaving group" means a group capable of separating itself from the rest of the molecule under the reaction conditions, so that another reagent reacts with the rest of the molecule to form a new bond with the carbon atom initially carrying the leaving group. The nature of the leaving group is not limited, and any leaving group known to the skilled person may be appropriate. Examples include sulphonates, such as mesylate or tosylate.

The intermediate (B6) can be prepared, according to techniques well known to the skilled person, from the following intermediate (B7):

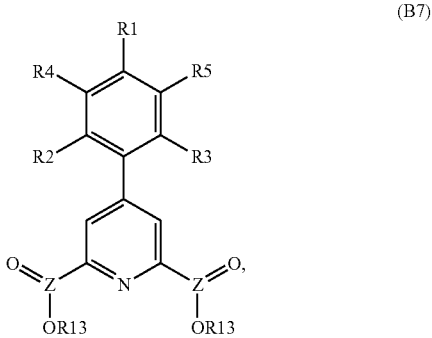

with —R1, —R2, —R3, —R4, —R5, —R13 and —Z— as defined for the intermediate (B6).

The intermediate (B7) can be synthesized from the reagent (B9), by forming a boronic acid (B8), followed by a Suzuki reaction with a dialkyl-4-halogeno-2,6-pyridinedicarboxylate:

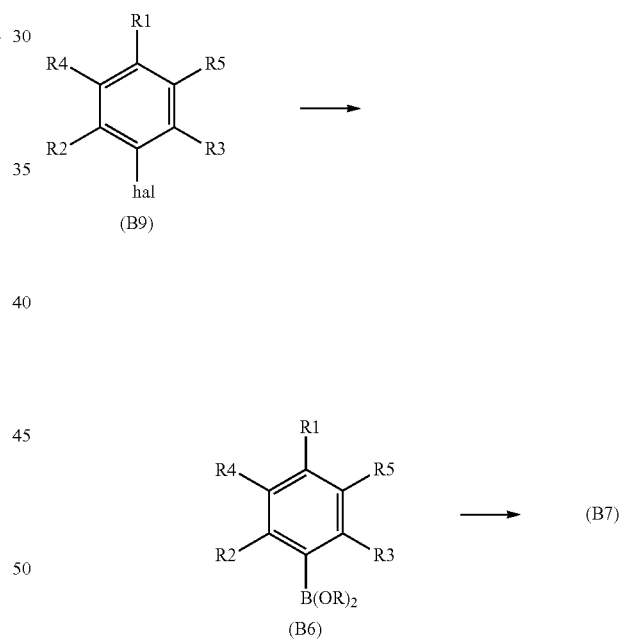

with —R1, —R2, —R3, —R4 and —R5 as defined for the intermediate (B7) and -hal representing a halogen, such as —Br, —Cl or —I.

According to a second embodiment, -Chrom1' and -Chrom2' are identical, and -Chrom3' is different from -Chrom1' and -Chrom2'. According to this embodiment, the chelating agent of formula (m) can be prepared by alkylation of the intermediate (I') with the intermediate of formula (B6"), with —R1", —R2", —R3", —R4", —R5", —R13", —Z" and -LG" as defined respectively for —R1, —R2, —R3, —R4, —R5, —R13, —Z and -LG for the chelating agent of formula (I):

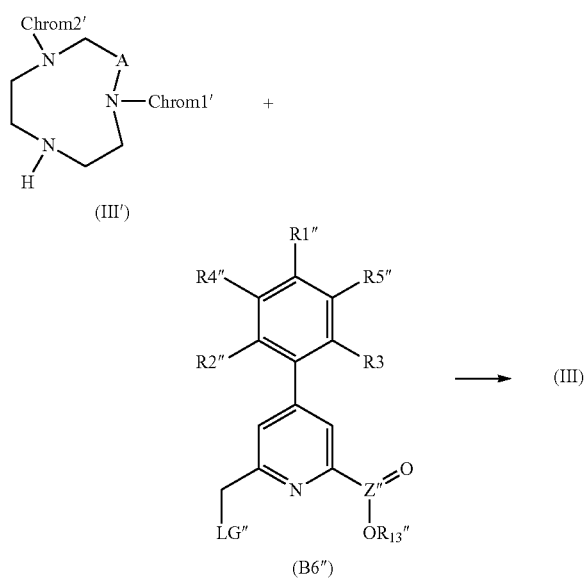

(III')

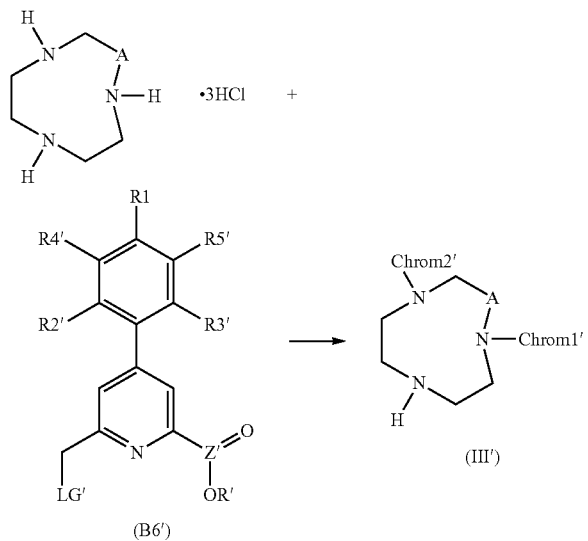

The intermediate (III') can be prepared by alkylation of TACN.3HCl ring with the intermediate of formula (B6'), with —R1', —R2', —R3', —R4', —R5', —R13', —Z' and -LG' as defined respectively for —R1, —R2, —R3, —R4, —R5, —R13, —Z and -LG for the chelating agent (m):

Advantageously, one of the three amine functions of the TACN.3HCl ring is protected, via a protecting group of the amine functions, prior to the alkylation step with the intermediate of formula (B6'); a subsequent deprotection step allowing the intermediate (III') to be generated.

The intermediates (B6') and (B6") can be obtained in a similar way to the intermediate (B6).

The formula (II) describes the family of lanthanide complexes resulting from the coordination of a chelating ligand of formula (IV) after deprotection and release of carboxylic acid functions. For the synthesis of these compounds, reference can be made in particular to applications WO 2013/026790 and WO 2013/092992 by Takalo.

Finally, the invention relates to a process for detecting a biomolecule comprising detecting the luminescence of a conjugate of said biomolecule with a luminescent complex as defined in the context of the invention, comprising a reactive group, and obtained by coupling said biomolecule with said luminescent complex on its reactive group.

Figure 1:
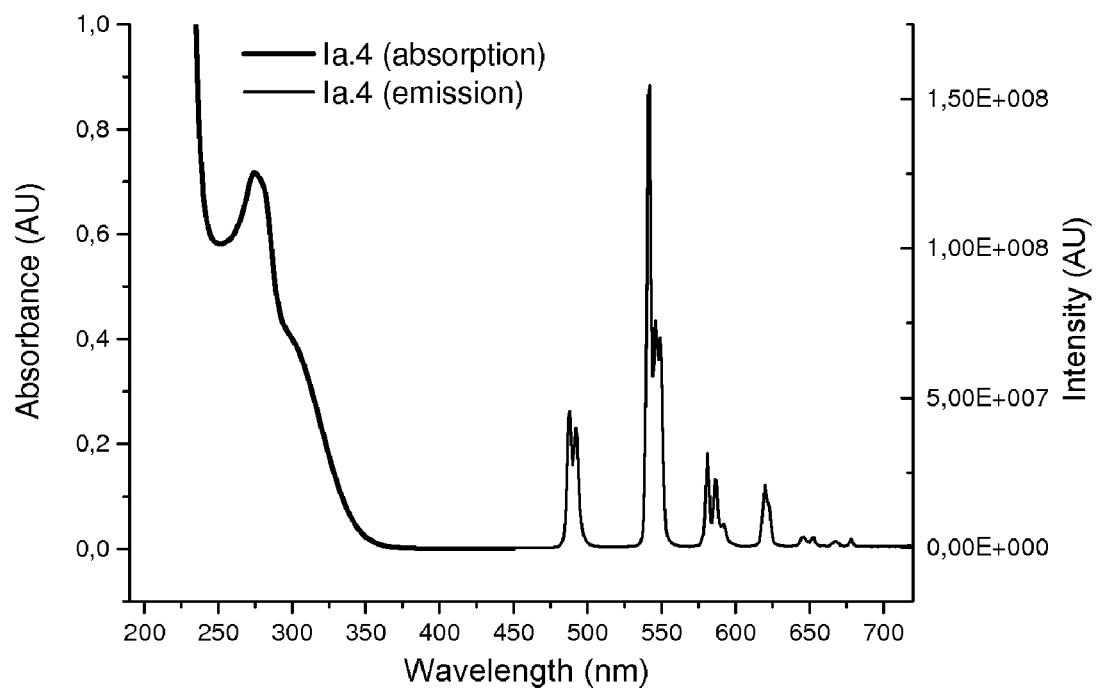
FIG. 1 shows the absorption and emission spectrum of complex Ia.4 in water at room temperature.

The examples below are intended to illustrate the invention but are not restrictive.

EXAMPLES

The abbreviations below are used in the following examples:

DCM: dichloromethane; DMF: dimethylformamide; DMSO: dimethylsulphoxide; Ms: mesyl; n.d.: not determined; PBS: phosphate buffered saline; PEG: polyethylene glycol; PFA: paraformaldehyde; quant.: quantitative; TACN: triazacyclononane; THF: tetrahydrofuran; Ts: tosyl General Information:

The NMR ($^1$H, $^{13}$C) spectra were recorded on a Bruker Avance device at a frequency of 300 MHz or 500.10 MHz, and 75 MHz or 125.75 MHz, for $^1$H and $^{13}$C respectively. Chemical shifts (δ) are expressed in parts per million (ppm) with respect to trimethylsilane used as an internal standard and using the solvents indicated. The coupling constants (J) are expressed in Hz and the following notations are used: s (singlet), br (broad), d (doublet), t (triplet), dd (doublet of doublets), m (multiplet). The high-resolution mass spectra were recorded at the Lyon Common Mass Spectrometry Centre (Claude Bernard Lyon University, Lyon, France) on a MicroTOFQII instrument equipped with a positive ESI source. Thin layer chromatography was performed on silica gel plates on aluminium foil (silica gel, Fluka) and revealed using a UV lamp (λ=254 or 365 nm) or by staining. Purifications were carried out by chromatographic column on silica gel (silica gel 0.035-0.070 mm, 60 Å). The solvents used for the reactions were purchased from Aldrich or Acros Organics as dry or extra dry solvents and stored on 3 Å molecular sieves and the reagents used were purchased from Aldrich, Acros Organics or Alfa Aesar. The UV/Vis absorption spectra were recorded on a JASCO V670 spectrometer; the emission spectra on a JOBIN-YVON fluorolog 3 spectrofluorimeter. Retention times were performed on an Agilent Technologies 1260 device equipped with a Waters XBridge RP-C18 column (3.5 nm, 4.6×100 mm). The chromatographic system used is 0.25 M ammonium formate-MeCN (v/v) as eluents: isocratic 15% MeCN (2 min), linear gradient 15 to 100% MeCN (16 min), isocratic 100% MeCN (4 min), at a rate of 1 mL/min, UV detection at 210 and 252 nm. Cellular imaging tests were performed using a solution concentrated in complex in DMSO to obtain a final complex concentration in the order of 1·10$^5$ M in cellular medium (PBS) with <1% DMSO. The T24 cells are prefixed to the PFA. The biphotonic absorption spectra were performed with a confocal laser scanning microscope LSM710 NLO (Carl Zeiss).

A. Preparation of the Complexes

Example 1: Europium Complexes Ia-Ie

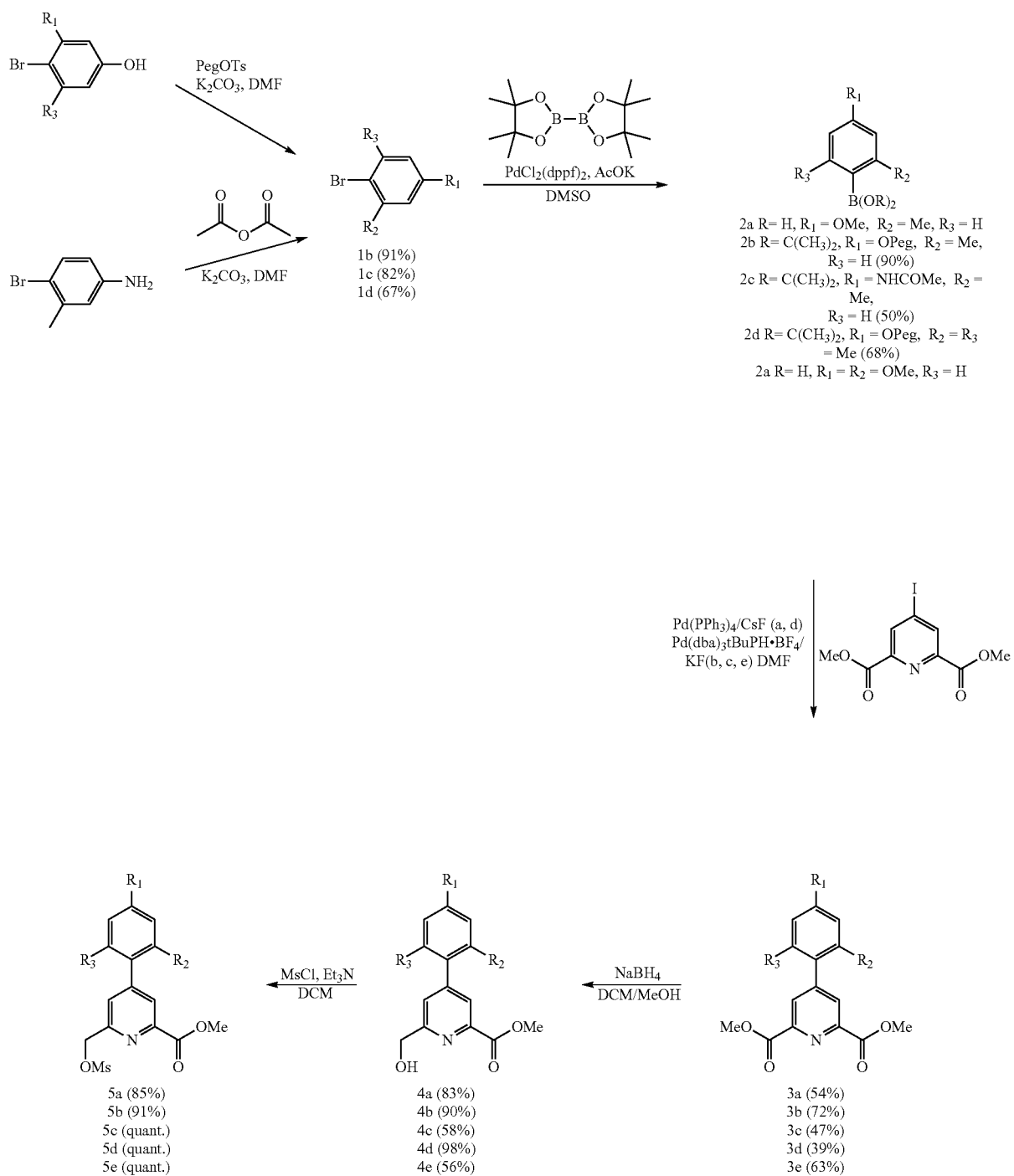

Compounds 1a (4-bromo-3-methylanisole), 1e (1-bromo-3,5-dimethoxybenzene) and 2e (2,4-dimethoxyphenylboronic acid) are commercially available. Compounds 1b and 1d are prepared from the corresponding phenol, while compound 1c is prepared from the corresponding aniline. Boronic acids 2a-2d are then obtained according to a procedure well known to the skilled person. The compounds 3a-e are obtained by a Suzuki coupling reaction with dimethyl-4-iodopicolinate. Then, a reduction and mesylation reaction is used to isolate the compounds 5a-e.

Scheme 2: Synthesis of complexes Ia-Ie
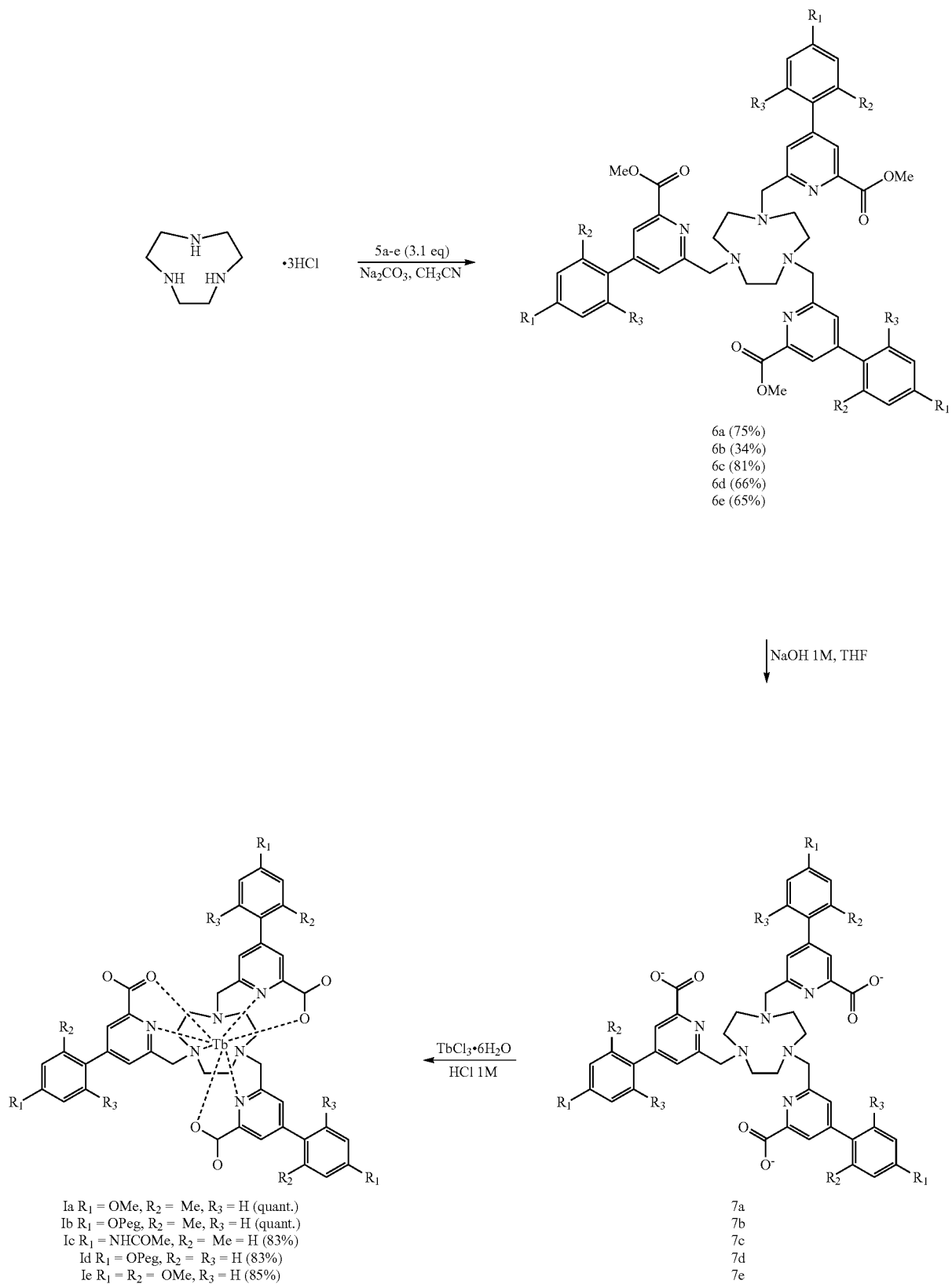

An alkylation reaction of TACN.3HCl with mesylate derivatives 5a-e under conventional alkylation conditions, followed by a step of deprotection of carboxylic acid functions, results in the lanthanide complexes Ia-Ie.

Compound 1b

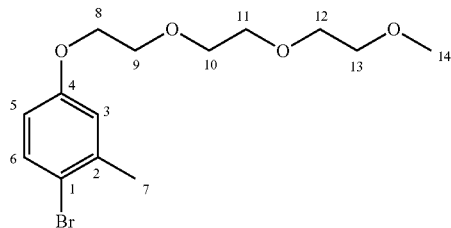

4-Bromo-3-methylphenol (1.0 g, 5.3 mmol) and $K_2CO_3$ (3.7 g, 27 mmol) are dried under vacuum then solubilized in dry DMF (20 mL). After 30 minutes, triethylene glycol methyl ether tosylate (2.55 g, 8 mmol) is added to the Schlenk flask. The reaction mixture is stirred at 80° C. for 5 days. The solution is then filtered on sintered P3, rinsed with $CH_2Cl_2$ and concentred under vacuum. The milieu is diluted in AcOEt/$Et_2O$ and washed with $H_2O$ and $NaCl_{sat}$. The organic phase is dried over $Na_2SO_4$, filtered and evaporated. The crude product is then purified on a chromatographic column ($SiO_2$, $CH_2Cl_2$/AcOEt, 90/10 to 80/20) to give the pure product as colourless oil (1.62 g, 91%). $R_f$ ($SiO_2$, $CH_2Cl_2$/AcOEt, 80/20)=0.53; $^1$H NMR (300 MHz, $CDCl_3$, δ): 7.38 (d, 1H, J=8.7 Hz, $H^6$), 6.81 (d, 1H, J=2.9 Hz, $H^3$), 6.62 (dd, 1H, $J_3$=8.7 Hz, $J_4$=2.9 Hz, $H^5$), 4.08 (t, 2H, J=4.6 Hz, $H^8$), 3.83 (t, 2H, J=4.6 Hz, $H^9$), 3.75-3.53 (m, 8H, $H^{10}$/$H^{11}$/$H^{12}$/$H^{13}$), 3.38 (s, 3H, $H^{14}$), 2.35 (s, 3H, $H^7$); $^{13}$C NMR (100 MHz, $CDCl_3$, δ): 158.2 ($C^4$), 138.9 ($C^2$), 132.9 ($C^6$), 117.4 ($C^3$), 115.8 ($C^5$), 113.8 ($C^5$), 72.1 ($C^{13}$), 71.0 ($C^{10}$), 70.8 ($C^{11}$), 70.8 ($C^{12}$), 69.8 ($C^9$), 67.8 ($C^8$), 59.2 ($C^{14}$), 23.3 ($C^7$); HRMS (ESI) calculated for $C_{14}H_{21}BrNaO_4$ 355.0515. Exp 355.0520 $[M+Na]^+$.

Compound 1c

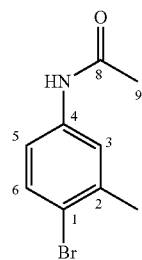

In a round-bottom flask, acetic anhydride (305 μL, 3.22 mmol) is added to a solution of 4-bromo-3-methylaniline (500 mg, 2.69 mmol) in dry $CH_2Cl_2$ under argon. The mixture is stirred at room temperature under argon until the complete reaction (TLC monitoring, petroleum ether/ethyl acetate, 80/20). After 4 h, the mixture is washed with $H_2O$ (3×). The organic phase is dried over $Na_2SO_4$, filtered on cotton and evaporated to obtain a white solid (506 mg, 82%). $R_f$($SiO_2$, $CH_2Cl_2$/AcOEt, 80/20)=0.46; $^1$H NMR (300 MHz, $CDCl_3$, δ): 7.45-7.42 (m, 2H, $H^6$/$H^3$), 7.19 (dd, 1H, $J_3$=8.6 Hz, $J_4$=2.4 Hz, $H^5$), 2.36 (s, 3H, $H^7$), 2.16 (s, 3H, $H^9$); $^{13}$C NMR (75 MHz, $CDCl_3$, δ): 169.0 ($C^8$), 138.5 ($C^4$), 137.2 ($C^1$), 132.6 ($C^3$), 122.4 ($C^6$), 119.6 ($C^2$), 119.2 ($C^5$), 24.5 ($C^9$), 23.1 ($C^7$); HRMS (ESI) calculated for $C_9H_{11}BrNO$ 228.0024. Exp 228.0019 $[M+H]^+$.

Compound 1d

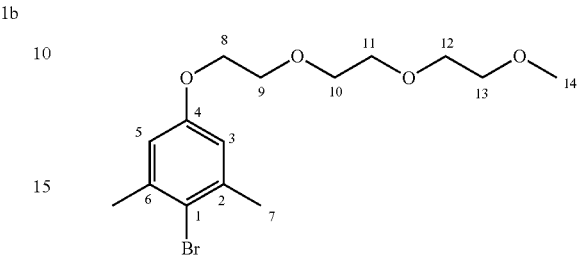

4-Bromo-3,5-dimethylphenol (1.30 g, 6.46 mmol) and $K_2CO_3$ (4.46 g, 9.68 mmol) are dried under vacuum then solubilized in dry DMF (12 mL). Argon bubbling is performed for 10 minutes and triethylene glycol methyl ether tosylate (3.08 g, 9.68 mmol) is added to the Schlenk flask. The reaction mixture is stirred at 80° C. for 3 days. A $CH_2Cl_2$/$H_2O$ extraction is then performed, then the organic phase is dried with $NaCl_{sat}$ and $Na_2SO_4$, filtered and evaporated. The crude product is then purified on a chromatographic column ($SiO_2$, $CH_2Cl_2$/AcOEt, 100/0 to 80/20) to give an oil of the pure product (1.5 g, 67%). $R_f$ ($SiO_2$, $CH_2Cl_2$/AcOEt, 95/5)=0.38; $^1$H NMR (300 MHz, $CDCl_3$, δ): 6.66 (s, 2H, $H^3$), 4.07 (t, 2H, J=4.7 Hz, $H^8$), 3.82 (t, 2H, J=4.7 Hz, $H^9$), 3.74-3.52 (m, 8H, $H^{10}$/$H^{11}$/$H^{12}$/$H^{13}$), 3.37 (s, 3H, $H^{14}$), 2.36 (s, 6H, $H^7$); $^{13}$C NMR (75 MHz, $CDCl_3$, δ): 157.4 ($C^4$), 139.2 ($C^1$), 118.5 ($C^{2/6}$), 114.7 ($C^{3/5}$), 72.1 ($C^{13}$), 71.0 ($C^{10}$), 70.8 ($C^{11}$), 70.7 ($C^{12}$), 69.8 ($C^9$), 67.7 ($C^8$), 59.2 ($C^{14}$), 24.1 ($C^7$); HRMS (ESI) calculated for $C_{15}H_{23}BrNaO_4$ 369.0672. Exp 369.0664 $[M+Na]^+$.

Compound 2a

The compound 2a was prepared according to the protocol described in "*Substituent Effects on Oxidation-Induced Formation of Quinone Methides from Arylboronic Ester Precursors*", Sheng Cao, Robin Christiansen, and Xiaohua Peng, *Chem. Eur. J.*, 2013, 19, 9050-9058.

Compound 2b

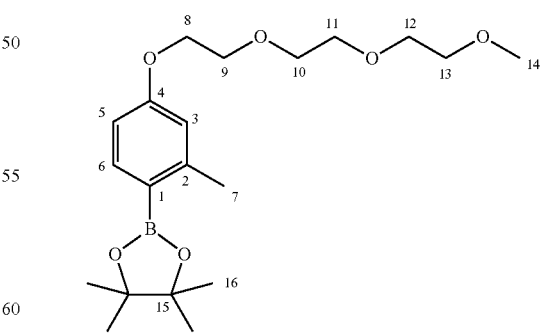

Dry potassium acetate (442 mg, 8.46 mmol) is solubilized in dry DMSO (15 mL) under argon then bis(dipicolinato) diboron (572 mg, 2.25 mmol) and 1b (500 mg, 1.50 mmol) are added. The solution is placed under argon bubbling for 20 minutes then $PdCl_2(dppf)_2$ (77 mg, 0.11 mmol) is added.

The reaction mixture is heated at 90° C. under argon and under stirring for 16 h. A serial extraction H₂O/Et₂O is then performed. The organic phases are combined, washed with NaCl$_{sat}$, dried over Na₂SO₄, filtered and evaporated under vacuum. The crude product is then purified on a column (SiO₂, CH₂Cl₂/AcOEt, 90/10 to 80/20) in order to obtain the pure product in the form of yellow oil (516 mg, 90%). R$_f$ (SiO₂, CH₂Cl₂/AcOEt, 80/20)=0.57; ¹H NMR (500 MHz, CDCl₃, δ): 7.69 (d, 1H, J=8.1 Hz, H⁶), 6.72-6.69 (m, 2H, H³/H⁵), 4.13 (t, 2H, J=4.7 Hz, H⁸), 3.85 (t, 2H, J=4.7 Hz, H⁹), 3.75-3.53 (m, 8H, H¹⁰/H¹¹/H¹²/H¹³), 3.38 (s, 3H, H¹⁴), 2.50 (s, 3H, H⁷), 1.32 (s, 12H, H¹⁶); ¹C NMR (125 MHz, CDCl₃, δ): 161.1 (C⁴), 147.3 (C²), 138.0 (C⁶), 120.6 (C¹), 116.4 (C³), 110.9 (C⁵), 83.3 (C¹⁵), 72.1 (C¹³), 71.0 (C¹⁰), 70.8 (C¹¹), 70.8 (C¹²), 69.9 (C⁹), 67.2 (C⁸), 59.2 (C¹⁴), 25.1 (C¹⁶), 22.6 (C⁷); HRMS (ESI) calculated for C₂₀H₃₃BNaO₆ 403.2262. Exp 403.2255 [M+Na]⁺.

Compound 2c

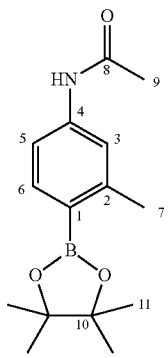

2c

Potassium acetate (515 mg, 5.25 mmol) is dried under vacuum/argon for 1 h then bis(pinacolato)diboron (668 mg, 2.63 mmol), dry DMSO (6 mL) and 1c (400 mg, 1.75 mmol) are added. Argon bubbling in the mixture is carried out for 20 min then PdCl₂(dppf)₂.CH₂Cl₂ (100 mg, 0.12 mmol) is added and the Schlenk flask is closed. The solution is heated at 90° C. under argon and under stirring for 19 h. After returning to room temperature, the mixture is filtered on sintered P3 and rinsed with Et₂O. Next is a serial extraction with H₂O/Et₂O. The organic phases are combined, dried over Na₂SO₄, filtered on cotton and evaporated. Slow evaporation CH₂Cl₂ gives rise to the formation of crystals which are washed several times with CH₂Cl₂ and dried under vacuum. ¹H NMR shows that the expected pure product (240 mg, 50%) was obtained. R$_f$ (SiO₂, CH₂Cl₂/AcOEt, 80/20)=0.61; ¹H NMR (300 MHz, CDCl₃, δ): 7.72 (d, 1H J=8 Hz, H⁵), 7.33 (s, 1H, H³), 7.30 (d, 1H, J=8 Hz, H⁶), 7.18 (s, 1H, NH), 2.51 (s, 3H, H⁷), 2.16 (s, 3H, H⁹), 1.33 (s, 12H, H¹¹); ¹³C NMR (75 MHz, CDCl₃, δ): 168.7 (C⁸), 146.4 (C²), 140.3 (C⁴), 137.1 (C⁶), 120.6 (C³), 115.9 (C⁵), 83.4 (C¹⁰), 25.1 (C⁹), 25.0 (C¹¹), 22.4 (C⁷); HRMS (ESI) calculated for C₁₅H₂₃BNO₃ 276.1768. Exp 276.1762 [M+H]⁺.

Compound 2d

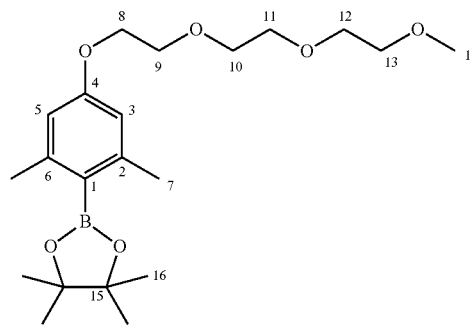

2d

Dry potassium acetate (830 mg, 8.46 mmol) is solubilized in dry DMSO (10 mL) under argon then bis(dipicolinato)diboron (1.07 g, 4.23 mmol) and 1d (979 mg, 2.82 mmol) are added. The solution is placed under argon bubbling for 20 minutes then PdCl₂(dppf)₂.CH₂Cl₂ (161 mg, 0.20 mmol) is added. The reaction mixture is heated at 90° C. under argon and under stirring for 40 h. A serial extraction H₂O/Et₂O is then performed. The organic phases are combined, washed with NaCl$_{sat}$, dried over Na₂SO₄, filtered and evaporated under vacuum. The crude product is then purified on a chromatographic column (SiO₂, CH₂Cl₂/AcOEt, 95/5 to 80/20) in order to obtain the pure product as oil (748 mg, 68%). R$_f$ (SiO₂, CH₂Cl₂/AcOEt, 80/20)=0.43; ¹H NMR (300 MHz, CDCl₃, δ): 6.51 (s, 2H, H³), 4.09 (t, 2H, J=4.7 Hz, H⁸), 3.82 (t, 2H, J=4.7 Hz, H⁹), 3.74-3.53 (m, 8H, H¹⁰/H¹¹/H¹²/H¹³), 3.37 (s, 3H, H¹⁴), 2.37 (s, 6H, H⁷), 1.36 (s, 12H, H¹⁶); ¹³C NMR (75 MHz, CDC₃, δ): 159.7 (C⁴), 144.5 (C²/⁶), 113.2 (C³/⁵), 83.5 (C¹⁵), 72.1 (C¹³), 70.9 (C¹⁰), 70.8 (C¹¹), 70.7 (C¹²), 69.9 (C⁹), 67.1 (C⁸), 59.1 (C¹⁴), 25.0 (C¹⁶), 22.7 (C⁷); HRMS (ESI) calculated for C₂₁H₃₅BNaO₆ 417.2423. Exp 417.2417 [M+Na]⁺.

Compound 3a

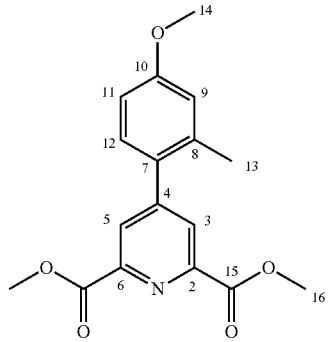

3a

In a Schlenk flask, dimethyl-4-iododipicolinate (300 mg, 0.934 mmol) and 2-methyl,4-methoxyphenylboronic acid (186 mg, 1.121 mmol) are solubilized in dry DMF (15 mL) under argon. After 30 minutes of argon bubbling in the mixture, caesium fluoride (355 mg, 2.335 mmol) and Pd(PPh₃)₄(cat.) are added. The reaction mixture is stirred at 90° C. under argon for 17 h. The mixture is then diluted in CH₂Cl₂ then extracted with H₂O. The chlorinated phase is evaporated and the aqueous phase is again extracted with AcOEt. The organic phase is washed with NaCl$_{sat}$, dried over Na$_2$SO$_4$, filtered and evaporated under vacuum. The crude product obtained is purified on 2 chromatographic columns (SiO$_2$, CH$_2$Cl$_2$/acetone, 90/10 then SiO$_2$, CH$_2$Cl$_2$/AcOEt 98/2 to 95/5) in order to obtain the pure product (159 mg, 54%). R$_f$ (SiO$_2$, CH$_2$Cl$_2$/acetone, 80/20)=0.82; $^1$H NMR (300 MHz, CDCl$_3$, δ): 8.28 (s, 2H, H$^{3/5}$), 7.24-7.20 (m, 1H, H$^{12}$), 6.87-6.85 (m, 2H, H$^{11}$/H$^9$), 4.04 (s, 6H, H$^{16}$), 3.86 (s, 3H, H$^{14}$), 2.32 (s, 3H, H$^{13}$); $^{13}$C NMR (125 MHz, CDCl$_3$, δ): 165.5 (C$^{15}$), 160.5 (C$^{10}$), 152.6 (C$^4$), 148.4 (C$^{2/6}$), 137.0 (C$^8$), 131.0 (C$^{12}$), 128.8 (C$^7$), 121.7 (C$^{3/5}$), 116.6 (C$^9$), 112.1 (C$^{11}$), 55.5 (C$^{14}$), 53.4 (C$^{16}$), 20.8 (C$^{13}$); HRMS (ESI) calculated C$_{17}$H$_{17}$NNaO$_5$ 338.0999. Exp 338.0990 [M+Na]$^+$.

Compound 3b

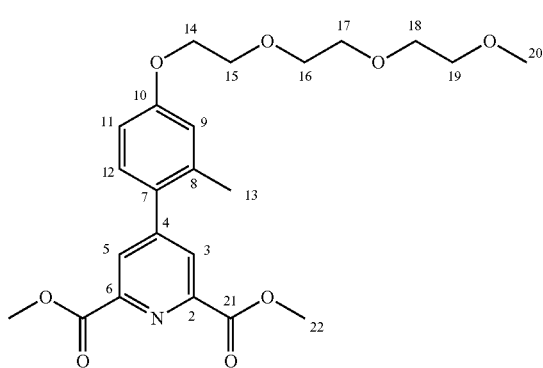

Dry dimethyl 4-iodo-2,6-pyridinedicarboxylate (344 mg, 1.07 mmol) is solubilized in dry DMF (12 mL) and 2b (448 mg, 1.18 mmol) is added under argon. The solution is placed under argon bubbling for 30 minutes then potassium fluoride (205 mg, 3.53 mmol) and Pd(dba)$_3$tBu$_3$PH.BF$_4$ (43 mg, 0.08 mmol) are added. The reaction mixture is placed at 80° C. under stirring and under argon for 40 h. A serial extraction AcOEt/H$_2$O is then performed. The organic phases are washed with NaCl$_{sat}$, dried over Na$_2$SO$_4$, filtered and evaporated under vacuum. The crude product is then purified on a chromatographic column (SiO$_2$, CH$_2$Cl$_2$/acetone, 95/5 to 90/10) to obtain the pure product as white solid (343 mg, 72%). R$_f$ (SiO$_2$, CH$_2$Cl$_2$/acetone, 90/10)=0.45; $^1$H NMR (500 MHz, CDCl$_3$, δ): 8.26 (s, 2H, H$^{15}$), 7.19 (d, 1H, J=8.3 Hz, H$^{12}$), 6.87 (d, 1H, J=2.3 Hz, H$^9$), 6.86 (dd, 1H, J$_3$=8.3 Hz, J$_4$=2.3 Hz, H$^{11}$), 4.17 (t, 2H, J=4.7 Hz, H$^{14}$), 4.03 (s, 6H, H$^{22}$), 3.86 (t, 2H, J=4.7 Hz, H$^{15}$), 3.76-3.54 (m, 8H, H$^{16}$/H$^{17}$/H$^{18}$/H$^{19}$), 3.38 (s, 3H, H$^{20}$), 2.30 (s, 3H, H$^{13}$); $^{13}$C NMR (125 MHz, CDCl$_3$, δ): 165.5 (C$^{21}$), 159.7 (C$^{10}$), 152.6 (C$^4$), 148.3 (C$^{2/6}$), 136.9 (C$^8$), 130.9 (C$^{12}$), 130.1 (C$^7$), 128.7 (C$^{3/5}$), 117.3 (C$^9$), 112.7 (C$^{11}$), 72.1 (C$^{19}$), 71.0 (C$^{16}$), 70.9 (C$^{17}$), 70.8 (C$^{18}$), 69.8 (C$^{15}$), 67.7 (C$^{14}$), 59.2 (C$^{20}$), 53.4 (C$^{22}$), 20.8 (C$^{13}$); HRMS (ESI) calculated for C$_{23}$H$_{30}$NO$_8$ 448.1966. Exp 448.1959 [M+H]$^+$.

Compound 3c

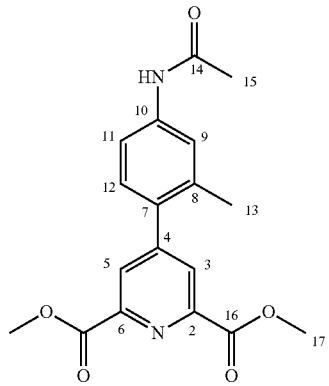

2c (200 mg, 0.73 mmol) and dimethyl 4-iodo-2,6-pyridinedicarboxylate (212 mg, 0.66 mmol) are first dried under vacuum/argon then dry DMF (15 mL) is added. The solution is degassed for 20 min under argon and potassium fluoride (126 mg, 2.18 mmol) and Pd(dba)$_3$tBu$_3$PH.BF$_4$ (27 mg, 0.05 mmol) are added. The mixture is placed at 80° C. under argon for 3 days. After returning to room temperature, CH$_2$Cl$_2$ is added and the organic phase is washed with H$_2$O (3×) and saturated NaCl (1×). The organic phase is dried over Na$_2$SO$_4$, filtered and evaporated under vacuum. After slow evaporation of a DCM/MeOH mixture, crystals are obtained and rinsed with a minimum of CH$_2$Cl$_2$ in order to obtain the pure product (107 mg, 47%). R$_f$ (SiO$_2$, CH$_2$Cl$_2$/MeOH, 95/5)=0.55; $^1$H NMR (300 MHz, CDCl$_3$, δ): 8.25 (s, 2H, H$^{3/5}$), 7.96 (s, 1H, NH), 7.55 (s, 1H, H$^9$), 7.48 (d, 1H, J=8.3 Hz, H$^{11}$), 7.19 (d, 1H, J=8.3 Hz, H$^{12}$), 4.00 (s, 6H, H$^{17}$), 2.26 (s, 3H, H$^{13}$), 2.19 (s, 3H, H$^{15}$); $^{13}$C NMR (75 MHz, CDCl$_3$, δ): 168.9 (C$^{14}$), 165.3 (C$^{16}$), 152.3 (C$^4$), 148.3 (C$^{2/6}$), 139.2 (C$^{10}$), 136.2 (C$^8$), 133.0 (C$^7$), 130.2 (C$^{12}$), 128.6 (C$^{3/5}$), 121.9 (C$^9$), 117.8 (C$^{11}$), 53.3 (C$^{17}$), 24.7 (C$^{15}$), 20.6 (C$^{13}$); HRMS (ESI) calculated for C$_{18}$H$_{19}$N$_2$O$_5$ 343.1288. Exp 343.1289 [M+H]$^+$.

Compound 3d

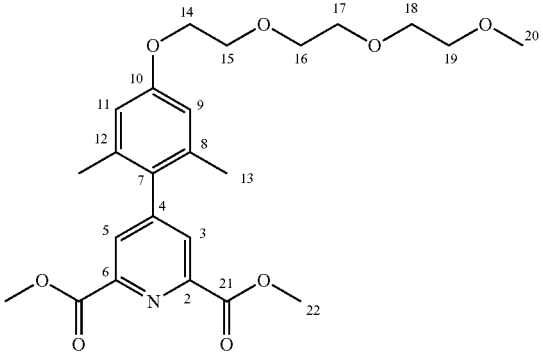

Dry dimethyl 4-iodo-2,6-pyridinedicarboxylate (144 mg, 0.45 mmol) is solubilized in dry DMF (5 mL) and 2d (195 mg, 0.50 mmol) is added under argon. The solution is placed under argon bubbling for 20 minutes then caesium fluoride (171 mg, 0.11 mmol) and Pd(PPh$_3$)$_4$ (52 mg, 0.05 mmol) are added. The reaction mixture is placed at 80° C. under stirring and under argon for 5 days. A serial extraction AcOEt/H$_2$O is then performed. The organic phases are washed with NaCl$_{sat}$, dried over Na$_2$SO$_4$, filtered and evaporated under vacuum. The crude product is then purified on a chromatographic column (SiO$_2$, CH$_2$Cl$_2$/acetone, 100% to 80/20) to obtain the pure product as oil (85 mg, 39%). R$_f$ (SiO$_2$, CH$_2$Cl$_2$/acetone, 95/5)=0.41; $^1$H NMR (300 MHz, CDCl$_3$, δ): 8.08 (s, 2H, H$^{15}$), 6.66 (s, 2H, H$^8$), 4.11 (t, 2H, J=4.6 Hz, H$^{14}$), 3.99 (s, 6H, H$^{22}$), 3.83 (t, 2H, J=4.6 Hz, H$^{15}$), 3.72-3.50 (m, 8H, H$^{16}$/H$^{17}$/H$^{18}$/H$^{19}$), 3.34 (s, 3H, H$^{20}$), 1.94 (s, 6H, H$^{13}$); $^{13}$C NMR (75 MHz, CDCl$_3$, δ): 165.2 (C$^{21}$), 158.7 (C$^{10}$), 152.5 (C$^4$), 148.7 (C$^{2/6}$), 136.5 (C$^{8/12}$), 130.0 (C$^7$), 129.6 (C$^{3/5}$), 114.0 (C$^{9/11}$), 72.0 (C$^{19}$), 70.9 (C$^{16}$), 70.7 (C$^{17}$), 70.6 (C$^{18}$), 69.7 (C$^{15}$), 67.4 (C$^{14}$), 59.0 (C$^{20}$), 53.2 (C$^{22}$), 21.0 (C$^{13}$).

Compound 3e

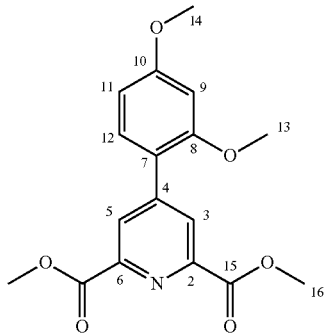

3e

In a Schlenk flask, dimethyl-4-iododipicolinate (200 mg, 0.623 mmol) and 2,4-dimethoxyphenylboronic acid (125 mg, 0.685 mmol) are solubilized in dry DMF (7 mL) under argon. After 30 minutes of argon bubbling in the mixture, potassium fluoride (119 mg, 2.056 mmol) and Pd(dba)$_3$ tBu$_3$PH.BF$_4$ (36 mg, 0.062 mmol) are added. The reaction mixture is stirred at 80° C. under argon for 19 h. The mixture is then diluted in a mixture AcOEt/Et$_2$O then extracted with H$_2$O then NaCl$_{sat}$. The organic phase is then dried over Na$_2$SO$_4$, filtered and evaporated under vacuum. The brown solid obtained is finally purified on a chromatographic column (SiO$_2$, AcOEt/EP, 20/80 to 60/40, solid deposition) in order to obtain the pure product in the form of a beige solid (131 mg, 63%). R$_f$ (SiO$_2$, EP/AcOEt, 60/40)=0.73; $^1$H NMR (300 MHz, CDCl$_3$, δ): 8.50 (s, 2H, H$^{35}$), 7.40 (d, 1H, J=8.5 Hz, H$^{12}$), 6.63 (dd, 1H, J$_3$=8.4 Hz, J$_4$=2.4 Hz, H$^{11}$), 6.58 (d, 1H, J=2.4 Hz, H$^9$), 4.04 (s, 6H, H$^{16}$), 3.88 (s, 3H, H$^{13}$), 3.87 (s, 3H, H$^{14}$); $^{13}$C NMR (100 MHz, CDC$_3$, δ): 165.8 (C$^{15}$), 162.5 (C$^{10}$), 158.2 (C$^8$), 149.2 (C$^4$), 148.1 (C$^{2/6}$), 131.6 (C$^{12}$), 128.4 (C$^{3/5}$), 118.6 (C$^7$), 105.5 (C$^9$), 99.2 (C$^{11}$), 55.8 (C$^{13}$), 55.7 (C$^{14}$), 53.4 (C$^{16}$); HRMS (ESI) calculated for C$_{17}$H$_{17}$NNaO$_6$ 354.0948. Exp 354.0937 [M+Na]$^+$.

Compound 4a

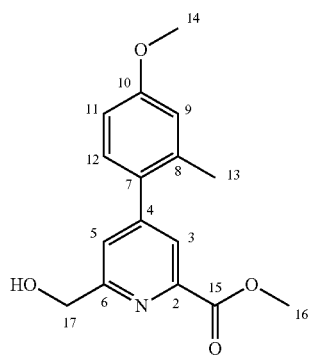

4a 3a (180 mg, 0.571 mmol) is solubilized in a CH$_2$Cl$_2$/MeOH mixture (2/3 mL) then cooled to 0° C. NaBH$_4$ (42 mg, 1.1 mmol) is then added and after 30 minutes, the reaction mixture is placed at room temperature for 4 h. The reaction is then quenched with a 1 M HCl solution. The organic phase is washed with H$_2$O (2×) then NaCl$_{sat}$, dried over Na$_2$SO$_4$, filtered and evaporated. The crude product is then purified on a chromatographic column (SiO$_2$, CH$_2$Cl$_2$/acetone 80/20 to 65/35) in order to obtain the pure product as pale yellow crystals (136 mg, 83%). R$_f$ (SiO$_2$, CH$_2$Cl$_2$/acetone, 80/20)=0.25; $^1$H NMR (500 MHz, CDCl$_3$, δ): 8.01 (s, 1H, H$^3$), 7.46 (s, 1H, H$^5$), 7.17 (d, 1H, J=8.8 Hz, H$^{12}$), 6.85-6.81 (m, 2H, H$^{11}$/H$^9$), 4.89 (d, 2H, J=4.6 Hz, H$^{17}$), 4.01 (s, 3H, H$^{16}$), 3.85 (s, 3H, H$^{14}$), 3.31 (t, 1H, J=4.6 Hz, OH), 2.29 (s, 3H, H$^{13}$); $^{13}$C NMR (125 MHz, CDCl$_3$, δ): 165.9 (C$^{15}$), 160.1 (C$^6$, C$^{10}$), 151.8 (C$^4$), 147.1 (C$^2$), 136.9 (C$^8$), 130.9 (C$^7$), 130.8 (C$^{12}$), 125.0 (C$^3$), 124.6 (C$^5$), 116.5 (C$^9$), 111.9 (C$^{11}$), 64.9 (C$^{17}$), 55.5 (C$^{14}$), 53.1 (C$^{16}$), 20.8 (C$^{13}$); HRMS (ESI) calculated for C$_{16}$H$_8$NO$_4$ 288.1230. Exp 288.1220 [M+H]$^+$. Calc for C$_{16}$H$_{17}$NNaO$_4$ 310.1050. Exp 310.1038 [M+Na]$^+$.

Compound 4b

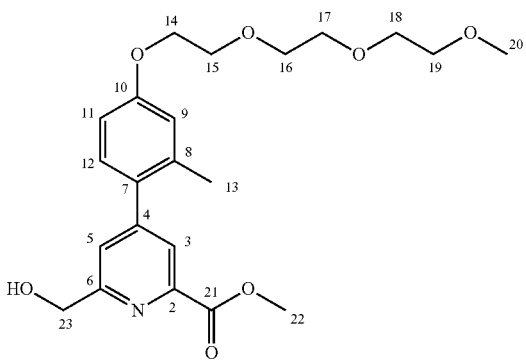

4b 3b (320 mg, 0.72 mmol) is solubilized in a CH$_2$Cl$_2$/MeOH mixture (2.5 mL/4.5 mL). After having placed the mixture at 0° C., NaBH$_4$ (30 mg, 0.79 mmol) is added and after 30 minutes, the solution is placed at room temperature under stirring for 3 h. The reaction is quenched by adding 1 M HCl solution. Then a CH$_2$Cl$_2$/H$_2$O extraction is carried out. The organic phase is washed with NaCl$_{sat}$, dried over Na$_2$SO$_4$, filtered and evaporated. A purification on a chromatographic column (SiO$_2$, CH$_2$Cl$_2$/MeOH, 98/2 to 97/3) is carried out in order to obtain the pure product as colourless oil (270 mg, 90%). R$_f$ (SiO$_2$, CH$_2$Cl$_2$/MeOH, 97/3)=0.22; $^1$H NMR (500 MHz, CDCl$_3$, δ): 7.99 (d, 1H, J=0.9 Hz, H$^3$), 7.47 (s, 1H, H$^5$), 7.15 (d, 1H, J=8.4 Hz, H$^{12}$), 6.85 (d, 1H, J=2.3 Hz, H$^9$), 6.83 (dd, 1H, J$_3$=8.4 Hz, J$_4$=2.3 Hz, H$^{11}$), 4.89 (d, 2H, J=3.9 Hz, H$^{23}$), 4.16 (t, 2H, J=4.7 Hz, H$^{14}$), 3.99 (s, 3H, H$^2$), 3.87 (t, 2H, J=4.7 Hz, H$^{15}$), 3.72-3.54 (m, 8H, H$^{16}$/H$^{17}$/H$^{18}$/H$^{19}$), 3.51 (m, 1H, OH), 3.37 (s, 3H, H$^{20}$), 2.27 (s, 3H, H$^{13}$); $^{13}$C NMR (125 MHz, CDCl$_3$, δ): 165.9 (C$^{21}$), 160.3 (C$^6$), 159.3 (C$^{10}$), 151.8 (C$^4$), 147.1 (C$^2$), 136.8 (C$^8$), 131.0 (C$^7$), 130.8 (C$^{12}$), 125.0 (C$^3$), 124.6 (C$^5$), 117.2 (C$^9$), 112.5 (C$^{11}$), 72.1 (C$^{19}$), 71.0 (C$^{16}$), 70.9 (C$^{17}$), 70.8 (C$^{18}$), 69.9 (C$^{15}$), 67.6 (C$^{14}$), 64.9 (C$^{23}$), 59.2 (C$^{20}$), 53.1 (C$^{22}$), 20.8 (C$^{13}$); HRMS (ESI) calculated for C$_{22}$H$_{30}$NO$_7$ 420.2017. Exp 420.2015 [M+H]$^+$.

Compound 4c

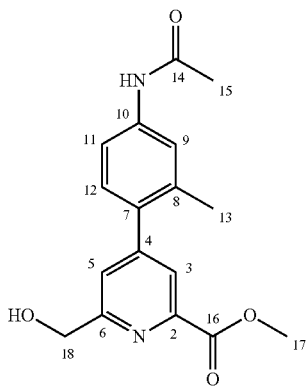

4c 3c is solubilized in a CH$_2$Cl$_2$/MeOH mixture and NaBH$_4$ is added at 0° C. After 5 minutes, the solution is left at room temperature and the monoreduction is monitored by TLC (SiO$_2$, DCM/MeOH, 95/5). At the end of 2.5 h, the reaction is quenched with 1 M HCl. The organic phase is then washed with H$_2$O and NaCl$_{sat}$, then dried over Na$_2$SO$_4$, filtered and evaporated. The crude product is purified on a chromatographic column (SiO$_2$, DCM/MeOH, 95/5) and a white powder is obtained (56 mg, 58%). R$_f$(SiO$_2$, CH$_2$Cl$_2$/MeOH, 95/5)=0.30; $^1$H NMR (300 MHz, CDCl$_3$, δ): 7.98 (s, 1H, H$^3$), 7.48 (m, 2H, H$^4$/H$^9$/NH), 7.42 (d, 1H, J=8.3 Hz, H$^{11}$), 7.17 (d, 1H, J=8.3 Hz, H$^{12}$), 4.90 (s, 2H, H$^{18}$), 4.00 (s, 6H, H$^{17}$), 3.57 (s, 1H, OH), 2.26 (s, 3H, H$^{13}$), 2.20 (s, 3H, H$^{15}$); $^{13}$C NMR (75 MHz, CDCl$_3$, δ): 168.7 (C$^{14}$), 165.8 (C$^{16}$), 160.4 (C$^6$), 151.4 (C$^4$), 147.1 (C$^2$), 138.6 (C$^{10}$), 136.2 (C$^8$), 134.2 (C$^7$), 130.2 (C$^{12}$), 124.7 (C$^3$), 124.4 (C$^5$), 121.9 (C$^9$), 117.7 (C$^{11}$), 64.9 (C$^{18}$), 53.1 (C$^{17}$), 24.8 (C$^{15}$), 20.6 (C$^{13}$); HRMS (ESI) calculated for C$_{17}$H$_{19}$N$_2$O$_4$ 315.1339. Exp 315.1342 [M+H]$^+$.

Compound 4d

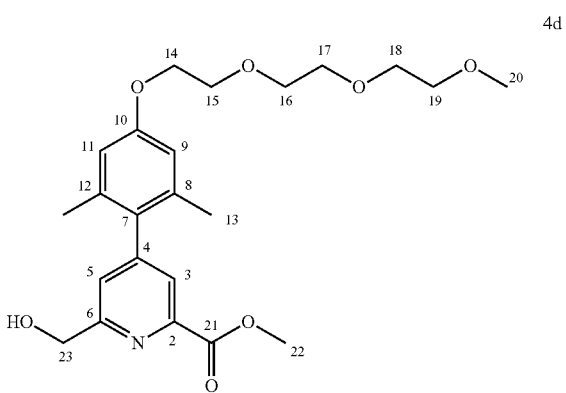

4d 3d (136 mg, 0.29 mmol) is solubilized in a CH$_2$Cl$_2$/MeOH mixture (50/50, 4 mL). After having placed the mixture at 0° C., NaBH$_4$ (42 mg, 1.11 mmol) is added (brown colouring of the solution) and after 20 minutes, the solution is placed at room temperature under stirring for 6 h. The reaction is quenched by adding 1 M HCl solution (4 mL). Then a CH$_2$Cl$_2$/H$_2$O extraction is carried out. The organic phase is washed with NaCl$_{sat}$, dried over Na$_2$SO$_4$, filtered and evaporated. A purification on a chromatographic column (SiO$_2$, CH$_2$Cl$_2$/AcOEt, 70/30 to 50/50 then 10% MeOH) is carried out in order to obtain the pure product (123 mg, 98%). R$_f$(SiO$_2$, CH$_2$Cl$_2$/AcOEt, 80/20)=0.32; $^1$H NMR (300 MHz, CDCl$_3$, δ): 8.08 (s, 1H, H$^3$), 7.79 (s, 1H, H$^5$), 6.63 (s, 2H, H$^9$), 4.87 (s, 2H, H$^{23}$), 4.09 (t, 2H, J=4.6 Hz, H$^{14}$), 3.93 (s, 3H, H$^2$), 3.81 (t, 2H, J=4.6 Hz, H$^{15}$), 3.72-3.49 (m, 8H, H$^{16}$/H$^{17}$/H$^{18}$/H$^{19}$), 3.33 (s, 3H, H$^2$), 1.93 (s, 6H, H$^{13}$); $^{13}$C NMR (75 MHz, CDCl$_3$, δ): 165.6 (C$^{21}$), 161.0 (C$^6$), 158.2 (C$^{10}$), 151.4 (C$^4$), 147.1 (C$^2$), 136.4 (C$^{8/12}$), 130.9 (C$^7$), 125.2 (C$^{3/5}$), 113.6 (C$^{9/11}$), 71.8 (C$^{19}$), 70.7 (C$^{16}$), 70.5 (C$^{17}$), 70.4 (C$^{18}$), 69.6 (C$^{15}$), 67.2 (C$^{14}$), 64.6 (C$^{23}$), 58.9 (C$^{20}$), 52.7 (C$^{22}$), 20.8 (C$^{13}$); HRMS (ESI) calculated for C$_{23}$H$_{32}$NO$_7$ 434.2173. Exp 434.2158 [M+H]$^+$.

Compound 4e

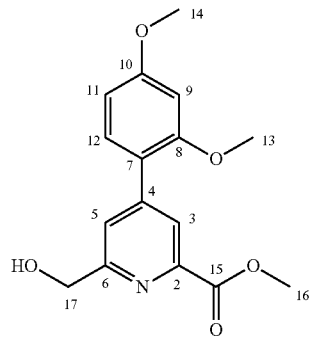

4e 3e (120 mg, 0.36 mmol) is solubilized in a CH$_2$Cl$_2$/MeOH mixture (2/3 mL) then cooled to 0° C. NaBH$_4$ (15 mg, 0.40 mmol) is then added and after 15 minutes, the reaction mixture is placed at room temperature for 4 h. The reaction is then quenched with a 1 M HCl solution. The organic phase is washed with H$_2$O (2×) then NaCl$_{sat}$, dried over Na$_2$SO$_4$, filtered and evaporated. The crude product is then purified on a chromatographic column (SiO$_2$, CH$_2$Cl$_2$/acetone 80/20) in order to obtain the pure product in the form of a beige solid (53 mg, 56%). R$_f$(SiO$_2$, CH$_2$Cl$_2$/acetone, 80/20)=0.17; $^1$H NMR (300 MHz, CDCl$_3$, δ): 8.21 (s, 1H, H$^3$), 7.67 (s, 1H, H$^5$), 7.33 (d, 1H, J=8.3 Hz, H$^{12}$), 6.60 (dd, 1H, J$_3$=8.3 Hz, J$_4$=2.4 Hz, H$^{11}$), 6.57 (d, 1H, J=2.4 Hz, H$^9$), 4.87 (d, 2H, J=4.5 Hz, H$^{17}$), 4.00 (s, 3H, H$^{16}$), 3.87 (s, 3H, H$^{13}$), 3.84 (s, 3H, H$^{14}$), 3.42 (br, 1H, OH).

Compound 5a

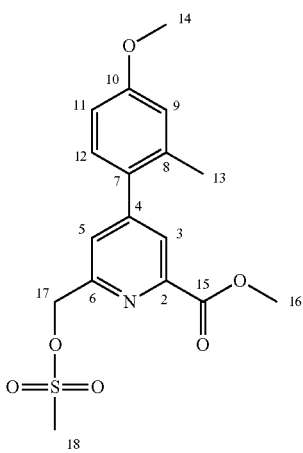

5a 4a (126 mg, 0.439 mmol) is solubilized in dry CH$_2$Cl$_2$ (4 mL) and triethylamine (180 μL, 1.317 mmol) is added. After having placed the mixture at 0° C., mesyl chloride (50 μL, 0.702 mmol) is added and after 5 minutes, the reaction mixture is placed at room temperature for 30 minutes. The organic phase is washed with H$_2$O, then dried over Na$_2$SO$_4$, filtered and evaporated to give a yellow oil used with purification for the following step (137 mg, 85%). R$_f$(SiO$_2$, CH$_2$Cl$_2$/MeOH, 95/5)=0.83; $^1$H NMR (300 MHz, CDCl$_3$, δ): 8.08 (s, 1H, H$^3$), 7.62 (s, 1H, H$^5$), 7.18 (m, 1H, H$^{12}$), 6.86-6.82 (m, 2H, H$^{11}$/H$^9$), 5.47 (s, 2H, H$^{17}$), 4.02 (s, 3H, H$^{16}$), 3.85 (s, 3H, H$^{14}$), 3.16 (s, 3H, H$^{18}$), 2.30 (s, 3H, H$^{13}$).

Compound 5b

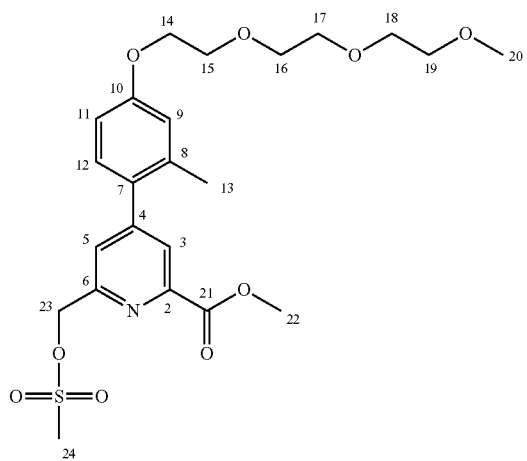

5b 4b (282 mg, 0.67 mmol) is solubilized in CH$_2$Cl$_2$ (8 mL) then triethylamine (280 μL, 2.02 mmol) is added. The mixture is placed at 0° C. then mesyl chloride (80 μL, 1.08 mmol) is added. After 5 minutes, the reaction mixture is placed at room temperature for 30 minutes. The organic phase is washed with H$_2$O then the aqueous phases are re-extracted with CH$_2$Cl$_2$. The organic phases are combined, dried over Na$_2$SO$_4$, filtered and evaporated under vacuum. The crude product is purified on a chromatographic column (SiO$_2$, CH$_2$Cl$_2$/MeOH, 98/2 to 96/4) in order to obtain the pure compound as a pale yellow oil (304 mg, 91%). R$_f$(SiO$_2$, CH$_2$Cl$_2$/MeOH, 95/5)=0.49; $^1$H NMR (500 MHz, CDCl$_3$, δ): 8.08 (d, 1H, J=1.5 Hz, H$^3$), 7.62 (d, 1H, J=1.5 Hz, H$^5$), 7.16 (d, 1H, J=8.3 Hz, H$^{12}$), 6.86 (d, 1H, J=2.6 Hz, H$^9$), 6.84 (dd, 1H, J$_3$=8.3 Hz, J$_4$=2.6 Hz, H$^{11}$), 5.46 (s, 2H, H$^2$), 4.17 (t, 2H, J=4.7 Hz, H$^{14}$), 4.01 (s, 3H, H$^2$), 3.88 (t, 2H, J=4.7 Hz, H$^{15}$), 3.76-3.55 (m, 8H, H$^{16}$/H$^{17}$/H$^{18}$/H$^{19}$), 3.38 (s, 3H, H$^{20}$), 3.16 (s, 3H, H$^{24}$), 2.28 (s, 3H, H$^{13}$); $^{13}$C NMR (125 MHz, CDCl$_3$, δ): 165.6 (C$^{21}$), 159.5 (C$^{10}$), 154.4 (C$^6$), 152.4 (C$^4$), 147.8 (C$^2$), 136.9 (C$^8$), 130.8 (C$^{12}$), 130.5 (C$^7$), 125.90 (C$^3$), 125.88 (C$^5$), 117.3 (C$^9$), 112.6 (C$^{11}$), 72.1 (C$^{19}$), 71.2 (C$^{23}$), 70.9 (C$^{16}$), 70.8 (C$^{17}$), 70.1 (C$^{18}$), 69.9 (C$^{15}$), 67.8 (C$^{14}$), 59.2 (C$^{20}$), 53.3 (C$^{22}$), 38.3 (C$^{24}$), 20.8 (C$^{13}$); HRMS (ESI) calculated for C$_{23}$H$_{32}$NO$_9$S 498.1792. Exp 498.1779 [M+H]$^+$.

Compound 5c

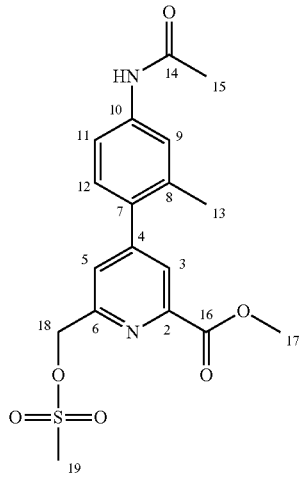

5c 4c (56 mg, 0.18 mmol) is solubilized in CH$_2$Cl$_2$ (4 mL) then triethylamine 75 μL, 0.53 mmol) is added. The mixture is placed at 0° C. and mesyl chloride (21 μL, 0.27 mmol) is added. After 5 minutes, the reaction is placed at room temperature under stirring for 40 minutes. A washing of the organic phase with H$_2$O is then carried out and the aqueous phases are re-extracted with CH$_2$Cl$_2$. The organic phases are combined, dried over Na$_2$SO$_4$, filtered and evaporated under vacuum. $^1$H NMR shows the obtaining of the pure product quantitatively (70 mg) and is used without further purification for the following step. R$_f$(SiO$_2$, CH$_2$Cl$_2$/MeOH, 95/5)= 0.64; $^1$H NMR (300 MHz, CDCl$_3$, δ): 8.04 (s, 1H, H$^3$), 7.89 (s, 1H, NH), 7.59 (s, 1H, H$^{45}$), 7.51 (s, 1H, H$^9$), 7.46 (d, 1H, J=8.3 Hz, H$^{11}$), 7.16 (d, 1H, J=8.3 Hz, H$^{12}$), 5.43 (s, 2H, H$^{18}$), 3.99 (s, 6H, H$^{17}$), 3.14 (s, 3H, H$^{19}$), 2.25 (s, 3H, H$^{13}$), 2.19 (s, 3H, H$^{15}$).

Compound 5d

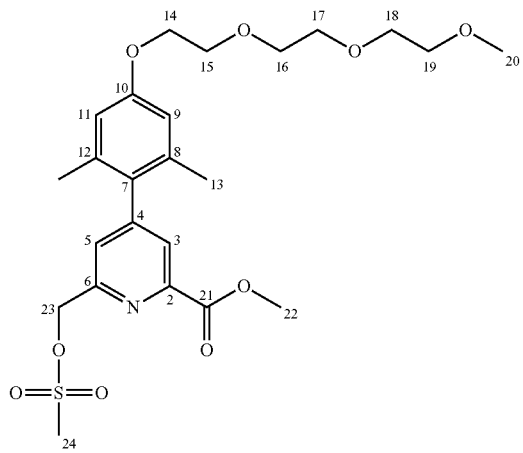

4d (123 mg, 0.28 mmol) is solubilized in $CH_2Cl_2$ (5 mL) then triethylamine (192 μL, 1.38 mmol) is added. The mixture is placed at 0° C. then mesyl chloride (53 μL, 0.68 mmol) is added. After 5 minutes, the reaction mixture is placed at room temperature for 30 minutes. The organic phase is washed with $H_2O$ then the aqueous phases are re-extracted with $CH_2Cl_2$. The organic phases are combined, dried over $Na_2SO_4$, filtered and evaporated under vacuum. The product obtained is used without further purification for the following step. $R_f$ ($SiO_2$, $CH_2Cl_2$/MeOH, 95/5)=0.76; $^1H$ NMR (300 MHz, $CDC_3$, δ): 7.90 (s, 1H, $H^3$), 7.45 (s, 1H, $H^5$), 6.66 (s, 2H, $H^9$), 5.44 (s, 2H, $H^{23}$), 4.12 (t, 2H, J=4.6 Hz, $H^{14}$), 3.97 (s, 3H, $H^2$), 3.83 (t, 2H, J=4.6 Hz, $H^{15}$), 3.74-3.51 (m, 8H, $H^{16}$/$H^{17}$/$H^{18}$/$H^{19}$), 3.35 (s, 3H, $H^{20}$), 3.13 (s, 3H, $H^{24}$), 1.95 (s, 6H, $H^{13}$); $^{13}C$ NMR (75 MHz, $CDCl_3$, δ): 165.3 ($C^{21}$), 158.6 ($C^{10}$), 154.7 ($C^6$), 152.3 ($C^4$), 148.0 ($C^2$), 136.5 ($C^{8/12}$), 130.4 ($C^7$), 126.6/126.5 ($C^{3/5}$), 113.9 ($C^{9/11}$), 71.9 (C19), 70.9 ($C^{16}$), 70.7 ($C^{17}$), 70.6 ($C^{18}$), 69.7 ($C^{15}$), 67.4 ($C^{14}$), 59.0 ($C^{20}$), 53.1 ($C^{22}$), 38.1 ($C^{23}$), 31.6 ($C^{24}$), 21.0 ($C^{13}$).

Compound 5e

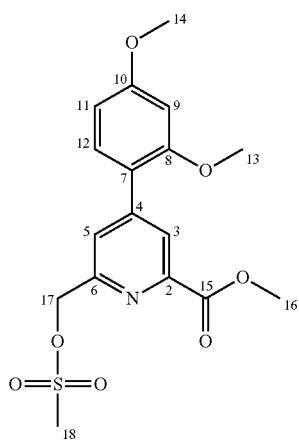

4e (60 mg, 0.198 mmol) is solubilized in $CH_2Cl_2$ (3 mL) and triethylamine (83 μL, 0.593 mmol) is added. After having placed the mixture at 0° C., mesyl chloride (24 μL, 0.317 mmol) is added and after 5 minutes, the reaction mixture is placed at room temperature for 30 minutes. The organic phase is washed with $H_2O$, then dried over $Na_2SO_4$, filtered and evaporated to give a yellow oil used with purification for the following step (76 mg, quant). $R_f$ ($SiO_2$, $CH_2Cl_2$/MeOH, 95/5)=0.76; $^1H$ NMR (300 MHz, $CDCl_3$, δ): 8.29 (s, 1H, $H^3$), 7.86 (s, 1H, $H^5$), 7.35 (d, 1H, J=8.4 Hz, $H^{12}$), 6.61 (dd, 1H, $J_3$=8.4 Hz, $J_4$=2.3 Hz, $H^{11}$), 6.57 (d, 1H, J=2.3 Hz, $H^9$), 5.46 (s, 2H, $H^{17}$), 4.02 (s, 3H, $H^{16}$), 3.87 (s, 3H, $H^{13}$), 3.85 (s, 3H, $H^{14}$), 3.14 (s, 3H, $H^{18}$).

Compound 6a

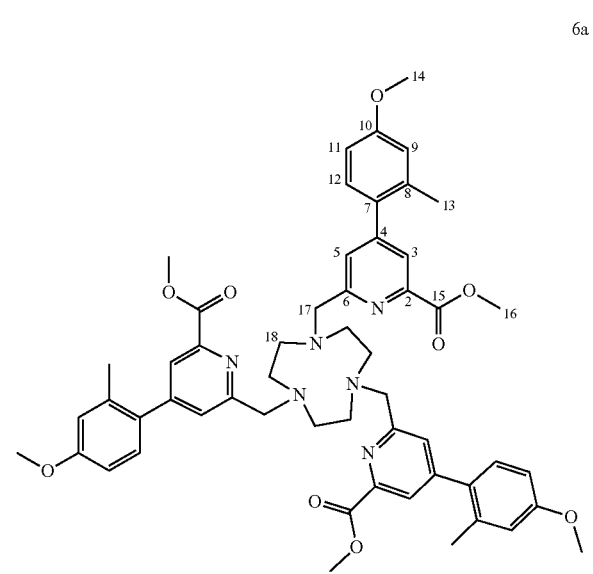

Triazacyclononane (27 mg, 0.115 mmol) and sodium carbonate (122 mg, 1.15 mmol) are solubilized in dry acetonitrile (7 mL). After 10 minutes at room temperature, 5a (130 mg, 0.356 mmol) is added and the reaction mixture is heated to 60° C. under stirring for 24 h then at room temperature for 24 h. The mixture is then filtered on sintered P3, rinsed with dry $CH_3CN$ and the mother liquors are evaporated. The crude product is purified on a chromatographic column ($Al_2O_3$, $CH_2Cl_2$/MeOH, 99/1 to 98/2) in order to obtain the pure product in the form of a pale yellow solid (81 mg, 75%). $R_f$ ($Al_2O_3$, $CH_2Cl_2$/MeOH, 95/5)=0.58; $^1H$ NMR (500 MHz, $CDCl_3$, δ): 7.94 (s, 3H, $H^3$), 7.68 (s, 3H, $H^5$), 7.09 (d, 3H, J=8.2 Hz, $H^{12}$), 6.79-6.75 (m, 6H, $H^9$/$H^{11}$), 3.98 (s, 9H, $H^{16}$), 3.97 (s, 6H, $H^{17}$), 3.83 (s, 9H, $H^{14}$), 2.92 (s, 12H, $H^{18}$), 2.23 (s, 9H, $H^{13}$); $^{13}C$ NMR (125 MHz, $CDCl_3$, δ): 166.2 ($C^{15}$), 161.1 ($C^6$), 159.9 ($C^{10}$), 151.2 ($C^4$), 147.3 ($C^2$), 136.7 ($C^8$), 131.1 ($C^7$), 130.8 ($C^{12}$), 127.0 ($C^5$), 124.7 ($C^3$), 116.3 ($C^9$), 111.8 ($C^{11}$), 64.8 ($C^{17}$), 56.0 ($C^{18}$), 55.4 ($C^{14}$), 53.1 ($C^{16}$), 20.9 ($C^{13}$); HRMS (ESI) calculated for $C_{54}H_{62}N_6O_9$ 469.2284. Exp 469.2273 $[M+2H]^{++}$.

Compound 6b

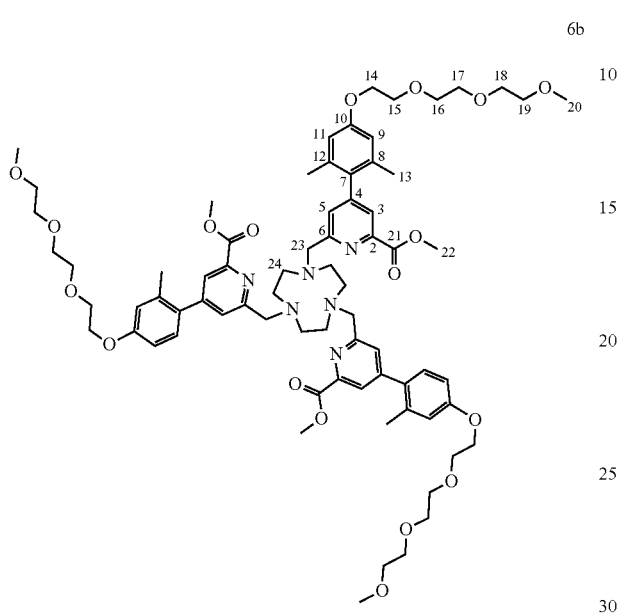

6b

Compound 6c

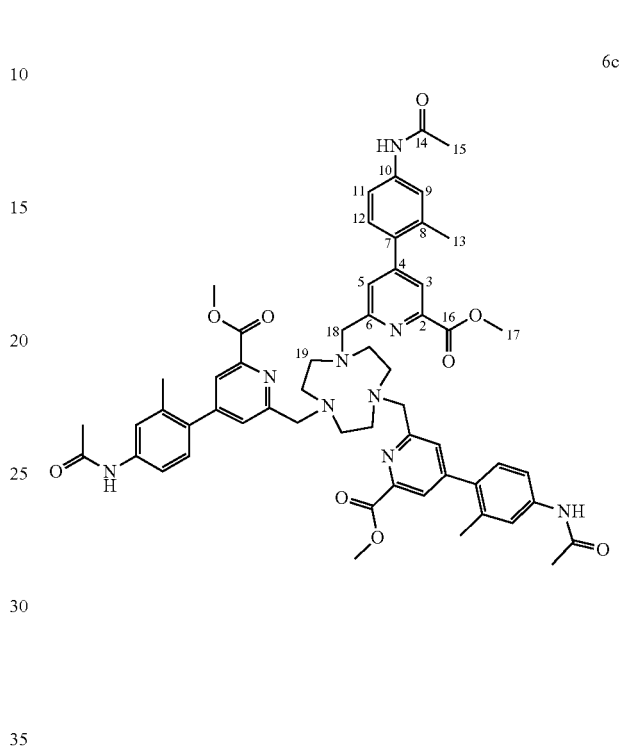

6c

Triazacyclononane (93 mg, 0.39 mmol) and sodium carbonate (414 mg, 3.91 mmol) are solubilized in dry acetonitrile (24 mL) under argon. After 10 minutes at room temperature, 5b (289 mg, 1.21 mmol) is added and the reaction mixture is heated to 60° C. under stirring for 24 h then at room temperature for 24 h. The mixture is then filtered on sintered P3, rinsed with dry $CH_3CN$ and the mother liquors are evaporated. The crude product is purified on a chromatographic column ($Al_2O_3$, $CH_2Cl_2$/MeOH, 99/1 to 95/5) in order to obtain the pure product in the form of a yellow oil (176 mg, 34%). $^1$H NMR (500 MHz, $CDC_3$, δ): 7.92 (d, 3H, J=1.1 Hz, $H^3$), 7.67 (s, 3H, $H^5$), 7.07 (d, 1H, J=8.4 Hz, $H^{12}$), 6.81 (d, 1H, J=2.4 Hz, $H^9$), 6.77 (dd, 1H, $J_3$=8.4 Hz, $J_4$=2.4 Hz, $H^{11}$), 4.14 (t, 6H, J=4.6 Hz, $H^4$), 3.96 (br s, 15H, $H^{23}$/$H^{22}$), 3.86 (t, 6H, J=4.6 Hz, $H^{15}$), 3.74-3.53 (m, 24H, $H^{16}$/$H^{17}$/$H^{18}$/$H^{19}$), 3.37 (s, 9H, $H^{20}$), 2.91 (br s, 12H, $H^{24}$), 2.21 (s, 9H, $H^{13}$); $^{13}$C NMR (125 MHz, $CDCl_3$, δ): 166.2 ($C^{21}$), 161.0 ($C^6$), 159.2 ($C^{10}$), 151.1 ($C^4$), 147.3 ($C^2$), 136.7 ($C^8$), 131.3 ($C^7$), 130.7 ($C^{12}$), 127.0 ($C^5$), 124.7 ($C^3$), 117.0 ($C^9$), 113.8 ($C^{11}$), 72.1 ($C^{19}$), 71.0 ($C^{16}$), 70.8 ($C^{17}$), 70.7 ($C^{18}$), 69.8 ($C^{15}$), 67.6 ($C^{14}$), 64.7 ($C^{23}$), 59.2 ($C^{20}$), 55.9 ($C^{24}$), 53.0 ($C^{22}$), 20.8 ($C^{13}$); HRMS (ESI) calculated for $C_{72}H_{98}N_6O_{18}$ 667.3463 Exp 667.34558 $[M+2H]^{2+}$.

5c dry (70 mg, 0.18 mmol) is solubilized in dry acetonitrile (3 mL) and $Na_2CO_3$ (67 mg, 0.63 mmol) is added as well as triazacyclononane (13.6 mg, 0.06 mmol). After argon bubbling in the mixture for 5 min, the reaction mixture is heated at 60° C. for 5 days. The mixture is then filtered on sintered P3, rinsed with dry $CH_3CN$ and the mother liquors are evaporated. The crude product is purified on a chromatographic column ($Al_2O_3$, $CH_2Cl_2$/MeOH, 96/4) in order to obtain the pure product in the form of a white powder (47 mg, 81%). $^1$H NMR (300 MHz, $CDCl_3$, δ): 8.94 (s, 3H, NH), 7.88 (s, 3H, $H^3$), 7.54-7.45 (m, 9H, $H^8$/$H^9$/$H^{10}$), 7.07 (d, 1H, J=8.3 Hz, $H^{12}$), 3.98 (m, 15H, $H^{18}$/$H^{17}$), 2.87 (s, 12H, $H^{19}$), 2.25 (s, 9H, $H^{13}$), 2.09 (s, 9H, $H^{15}$); $^{13}$C NMR (75 MHz, MeOD, δ): 171.8 ($C^{14}$), 166.9 ($C^{16}$), 162.4 ($C^6$), 152.8 ($C^4$), 148.3 ($C^2$), 140.7 ($C^{10}$), 136.9 ($C^8$), 134.9 ($C^7$), 131.0 ($C^{12}$), 128.6 ($C^3$), 124.4 ($C^5$), 123.0 ($C^9$), 118.9 ($C^{11}$), 65.0 ($C^{18}$), 57.0 ($C^{19}$), 53.3 ($C^{17}$), 24.05 ($C^{15}$), 20.9 ($C^{13}$); HRMS (ESI) calculated for $C_{57}H_{64}N_9O_9$ 1018.4822. Exp 1018.4782 $[M+H]^+$; $t_R$=8.33 min (method HPLC-MM-ACN, $H_2O$/$CH_3CN$ 85/15 to 0/100 in 16 min).

Compound 6d

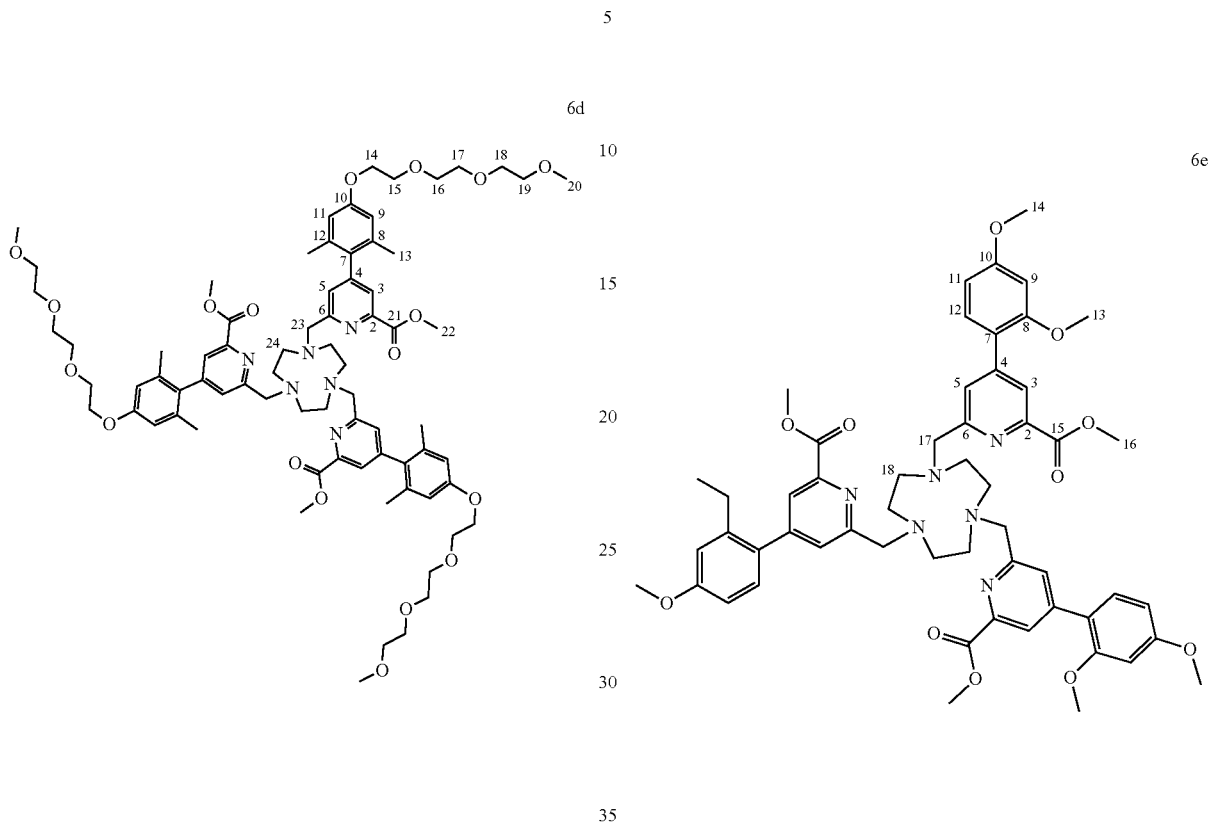

6d

Compound 6e

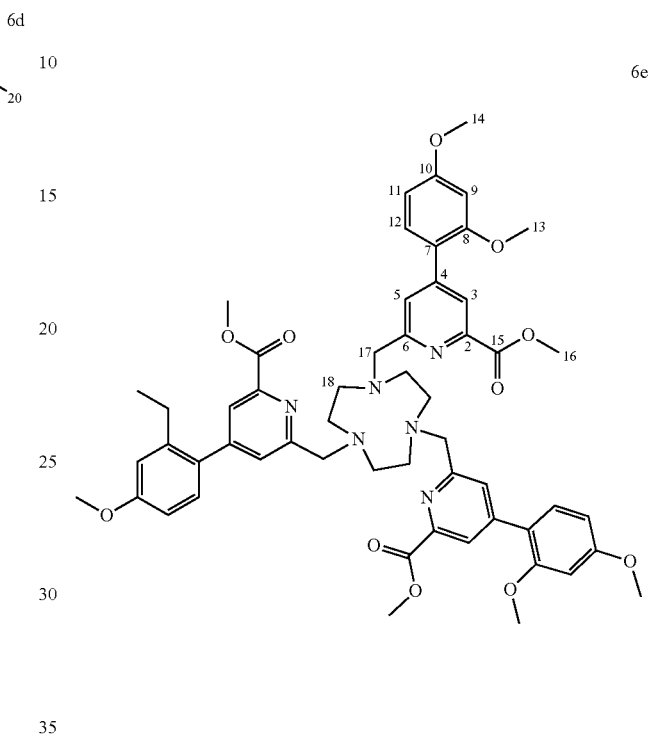

6e

Triazacyclononane (21.5 mg, 0.09 mmol) and sodium carbonate (95 mg, 0.90 mmol) are solubilized in dry acetonitrile (5 mL). After 5 minutes at room temperature, 5d (143 mg, 0.28 mmol) is added, argon bubbling is carried out for 5 minutes and the reaction mixture is heated to 60° C. under stirring for 4 days. The mixture is then filtered on sintered P3, rinsed with dry $CH_3CN$ and the mother liquors are evaporated. The crude product is purified on a chromatographic column ($Al_2O_3$, $CH_2Cl_2$/MeOH, 100% to 97/3) in order to obtain the pure product in the form of a white powder (82 mg, 66%). $^1H$ NMR (300 MHz, $CDCl_3$, δ): 7.77 (s, 3H, $H^3$), 7.47 (s, 3H, $H^5$), 6.64 (s, 6H, $H^9$), 4.12 (t, 6H, J=4.7 Hz, $H^{14}$), 3.94 (s, 9H, $H^2$), 3.91 (s, 6H, $H^3$), 3.84 (t, 6H, J=4.7 Hz, $H^{15}$), 3.74-3.52 (m, 24H, $H^{16}/H^{17}/H^{18}/H^{19}$), 3.35 (s, 9H, $H^{20}$), 2.82 (s, 12H, $H^{24}$), 1.91 (s, 18H, $H^{13}$); $^{13}C$ NMR (75 MHz, $CDCl_3$, δ): 166.0 ($C^{21}$), 161.4 ($C^6$), 158.3 ($C^{10}$), 151.0 ($C^4$), 147.5 ($C^2$), 136.5 ($C^{8/12}$), 131.3 ($C^7$), 127.8 ($C^5$), 125.3 ($C^3$), 113.8 ($C^{9/11}$), 72.0 ($C^{19}$), 70.9 ($C^{16}$), 70.7 ($C^{17}$), 70.6 ($C^{18}$), 69.8 ($C^{15}$), 67.4 ($C^{14}$), 64.6 ($C^{23}$), 59.1 ($C^{20}$), 55.6 ($C^{24}$), 52.9 ($C^{22}$), 21.0 ($C^{13}$); HRMS (ESI) calculated for $C_{75}H_{104}N_6O_{18}$ 688.3698. Exp 688.3686 $[M+2H]^{2+}$; $t_R$=13.09 min (method HPLC-MM-ACN, $H_2O$/$CH_3CN$ 85/15 to 0/100 in 16 min).

Triazacyclononane (15 mg, 0.064 mmol) and sodium carbonate (68 mg, 0.64 mmol) are solubilized in dry acetonitrile (4 mL). After 10 minutes at room temperature, 5e (76 mg, 0.198 mmol) is added and the reaction mixture is heated to 60° C. under stirring for 24 h then at room temperature for 5 days. The mixture is then filtered on sintered P3, rinsed with dry $CH_3CN$ and the mother liquors are evaporated. The crude product is purified on a chromatographic column ($Al_2O_3$, $CH_2C_2$/MeOH, 100% to 97/3) in order to obtain the pure product in the form of a white powder (41 mg, 65%). $R_f$($Al_2O_3$, $CH_2C_2$/MeOH, 95/5)=0.54; $^1H$ NMR (500 MHz, $CDCl_3$, δ): 8.15 (s, 3H, $H^3$), 7.92 (s, 3H, $H^5$), 7.25 (d, 3H, J=8.0 Hz, $H^{12}$), 6.54-6.49 (m, 6H, $H^9/H^{11}$), 3.99 (s, 6H, $H^{17}$), 3.97 (s, 9H, $H^{16}$), 3.84 (s, 9H, $H^{13}$), 3.75 (s, 9H, $H^{14}$), 2.99 (s, 12H, $H^{18}$); $^{13}C$ NMR (125 MHz, $CDCl_3$, δ): 166.5 ($C^{15}$), 161.9 ($C^{10}$), 160.9 ($C^6$), 158.0 ($C^8$), 147.8 ($C^4$), 147.2 ($C^2$), 131.4 ($C^{12}$), 126.6 ($C^5$), 124.4 ($C^3$), 119.9 ($C^7$), 105.3 ($C^9$), 99.2 ($C^{11}$), 65.0 ($C^{17}$), 56.2 ($C^{18}$), 55.7 ($C^{13}$), 55.6 ($C^{14}$), 53.0 ($C^{16}$).

Compound 7c

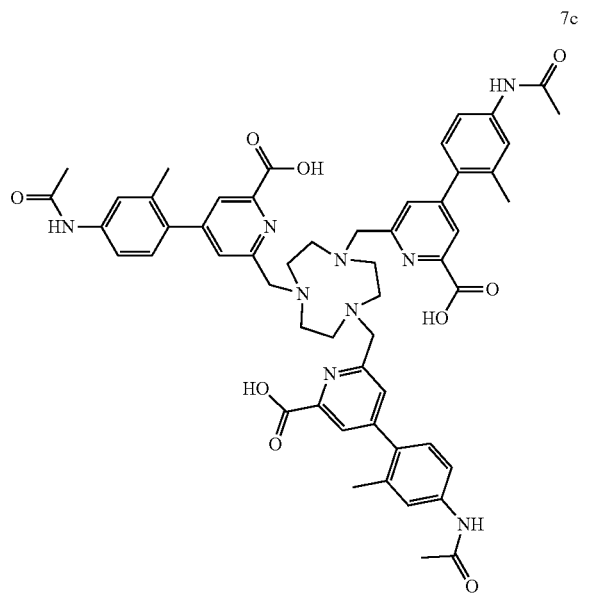

6c (47 mg, 0.05 mmol) is dissolved in THF (3 mL) then 1 M NaOH (3 mL) is added to pH>12. The reaction mixture is stirred at room temperature for 24 h. LC-MS monitoring is used to observe the complete deprotection of the methyl esters. The product is used for the complexation without further purification. HRMS (ESI) calculated for $C_{54}H_{55}N_9O_9$ 976.4352. Exp 976.4306 [M+H]$^+$; t=6.24 min (method HPLC-MM-ACN, $H_2O/CH_3CN$ 85/15 to 0/100 in 16 min).

Compound 7d

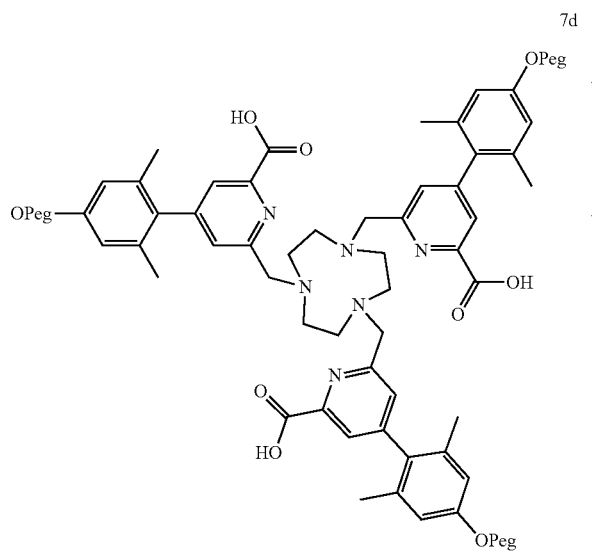

6d (38.7 mg, 0.028 mmol) is dissolved in tetrahydrofuran (3 mL) and 1 M NaOH (3 mL) is added to pH 14. The reaction mixture is stirred at room temperature for 6.5 h. Mass spectrometric monitoring shows the disappearance of the starting material. The mixture is used for the complexation step without further purification. HRMS (ESI) calculated for $C_{75}H_{98}N_6O_{18}$ 667.3463. Exp 667.3461 [M+2H]$^{2+}$; $t_R$=9.57 min (method HPLC-ESI-ACN, $H_2O/CH_3CN$ 85/15 to 0/100 in 16 min).

Complex Ia.1

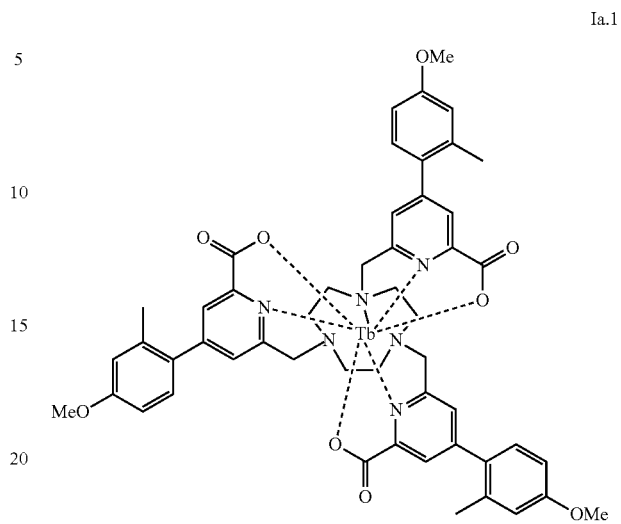

The ligand 6a (70 mg, 0.075 mmol) is dissolved in THF (10 mL) then 1 M NaOH (5 mL) is added and the solution is stirred at room temperature for 1.5 h. The pH is then adjusted to pH 4 with 1 M HCl (5 mL) and the mixture is concentrated under vacuum. The mixture is diluted with MeOH then the pH is adjusted to pH 8-9 aided by a solution of $Na_2CO_{3sat}$. Finally, $TbCl_3.6H_2O$ (84 mg, 0.224 mmol) is added and the reaction mixture is stirred at room temperature for 72 h. The mixture is concentrated under reduced pressure then the complex is precipitated by adding $H_2O$ (2×) and centrifuged to obtain a white solid corresponding to the terbium(III) complex (79 mg, quant). HRMS (ESI) calculated for $C_{51}H_{53}N_6O_9Tb$ 526.1558. Exp 526.1557 [M+2H]$^{++}$. Calc for $C_{51}H_{52}N_6O_9Tb$ 1051.3044. Exp 1051.3011 [M+H]$^+$.

Complex Ia.2

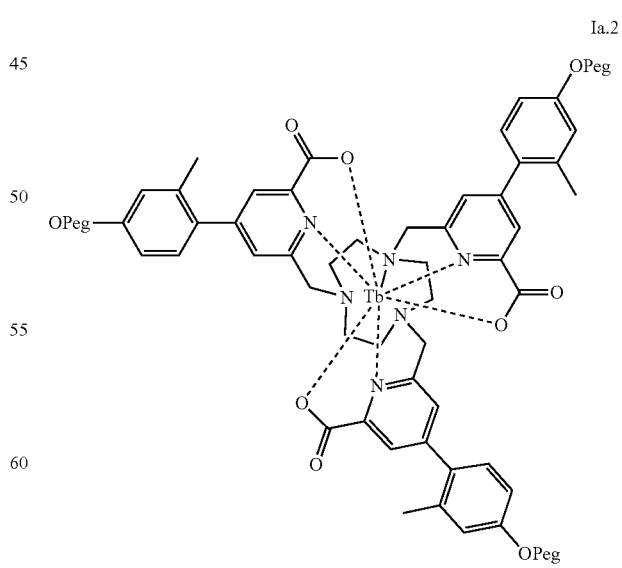

The ligand 6b (50 mg, 0.038 mmol) is solubilized in MeOH (5 mL) then 1 M NaOH (2 mL) is added and the solution is left under stirring at room temperature for 1 h. Then the pH is adjusted to pH 3~4 with 1 M HCl, then to pH ~7 with $Na_2CO_{3sat}$. $TbCl_3.6H_2O$ (21 mg, 0.056 mmol) is added and the solution is left at room temperature overnight. After concentration under reduced pressure, the mixture is purified by extractions/washes with $DCM/H_2O$, and the organic phase evaporated to give the product in the form of a pale yellow solid (55 mg, quant.). HRMS (ESI) calculated for $C_{69}H_{87}N_6Na_2O_{18}Tb$ 746.2557. Exp 746.2565 [M+2Na]$^{2+}$; $t_R$=9.65 min (method HPLC-MM, $H_2O/CH_3CN$ 85/15 to 0/100 in 16 min).

Complex Ia.3

Complex Ia.4

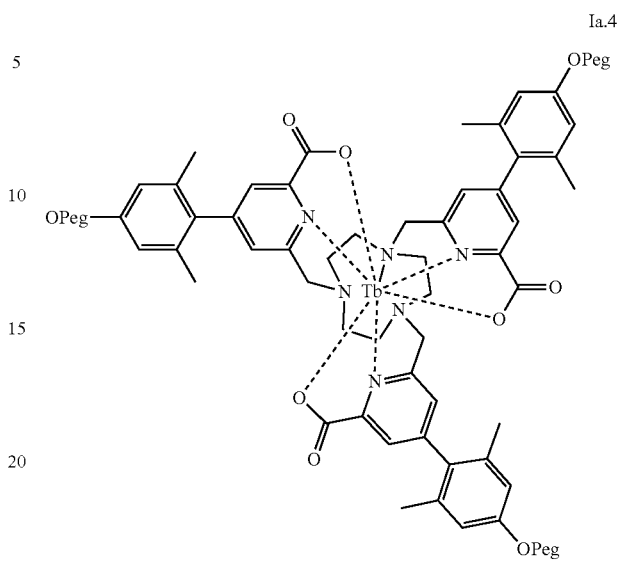

Ia.4

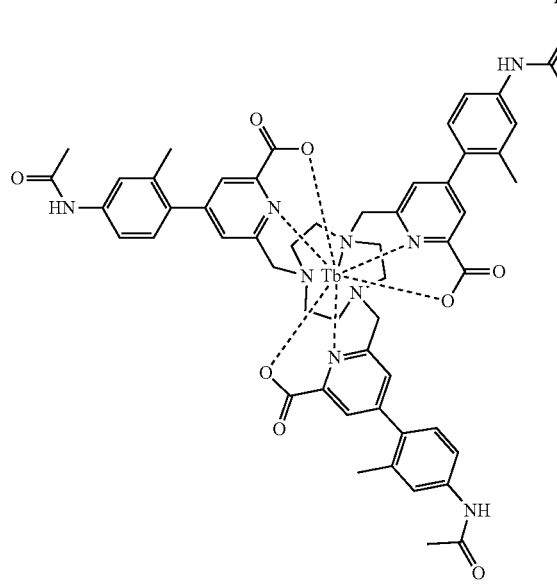

Ia.3

The pH of the solution 7d is adjusted to pH 6 with 1 M HCl then $TbCl_3.6H_2O$ (12 mg, 0.031 mmol) is added and the solution is left under stirring at room temperature for 6 days. THF is then evaporated and a $CH_2Cl_2/H_2O$ extraction is carried out. The organic phases are combined and evaporated to obtain the pure terbium(III) complex (38 mg, 90%). HRMS (ESI) calculated for $C_2H_{95}N_6O_{18}Tb$ 745.2973. Exp 745.2966 [M+2H]$^{2+}$, $C_{72}H_{94}N_6O_{18}TbNa$ 756.2882. Exp 756.2882 [M+H+Na]+; $t_R$=9.64 min (method HPLC-ESI-ACN-365, $H_2O/CH_3CN$ 85/15 to 0/100 in 16 min).

Complex 8 (outside the invention)

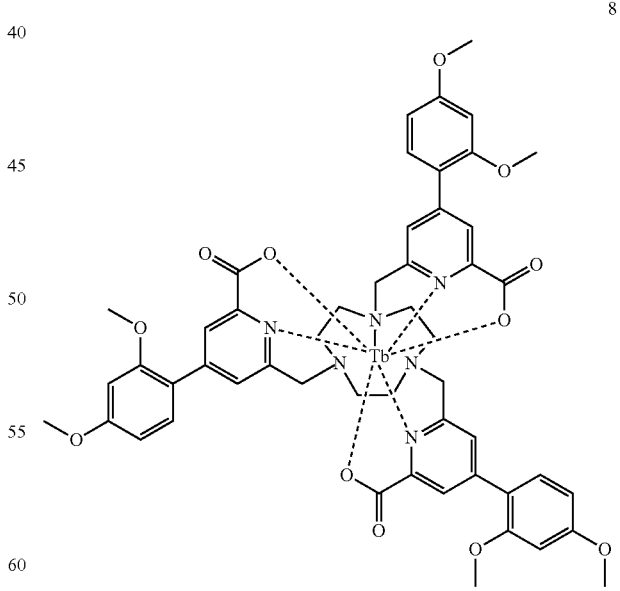

8

The pH of the solution of 7c is adjusted to pH b by adding solution of 1 M HCl then $TbCl_3.6H_2O$ is added at room temperature. The reaction mixture is stirred for 48 h then THF is evaporated under reduced pressure. The precipitate formed is centrifuged in $H_2O$ (3×) to remove excess salts present then the white solid is dried under vacuum (43 mg, 83%). HRMS (ESI) calculated for $C_{54}H_{55}N_9O_9Tb$ 1132.3371. Exp 1132.3323 [M+H]$^+$, $C_{54}H_{54}N_9O_9TbNa$ 1154.3190, Exp 1154.3133 [M+Na]$^+$; $t_R$=6.67 min (method HPLC-MM-ACN, $H_2O/CH_3CN$ 85/15 to 0/100 in 16 min).

The ligand 6e (31 mg, 0.032 mmol) is dissolved in MeOH (5 mL) then 1 M NaOH (2 mL) is added and the solution is stirred at room temperature for 2 h. The pH is then adjusted to pH 3-4 with 1 M HCl (2 mL) then to pH 7 aided by a solution of $Na_2CO_{3sat}$. $ThCl_3.6H_2O$ (18 mg, 0.047 mmol) is finally added and the reaction mixture is stirred at room temperature for 14 h. The mixture is concentrated under reduced pressure then the complex is precipitated by adding $H_2O$ (2×) and centrifuged. Then the solid obtained is again precipitated in $Et_2O$ and centrifuged to obtain a new white precipitate corresponding to the terbium(III) complex (30 mg, 85%). MS Calc for $C_{51}H_{53}N_6O_{12}Tb$ 550.1488. Exp 550.1482 $[M+2H]^{2+}$; calc for $C_{51}H_{52}N_6NaO_{12}Tb$ 561.1392. Exp 561.1405 $[M+H+Na]^{2+}$; calc for $C_{51}H_{51}N_6Na_2O_{12}Tb$ 572.1301. Exp 572.1323 $[M+2Na]^{2+}$.

Example 2: Dysprosium Complex Ia.5 and Ia.6

Complex Ia.5

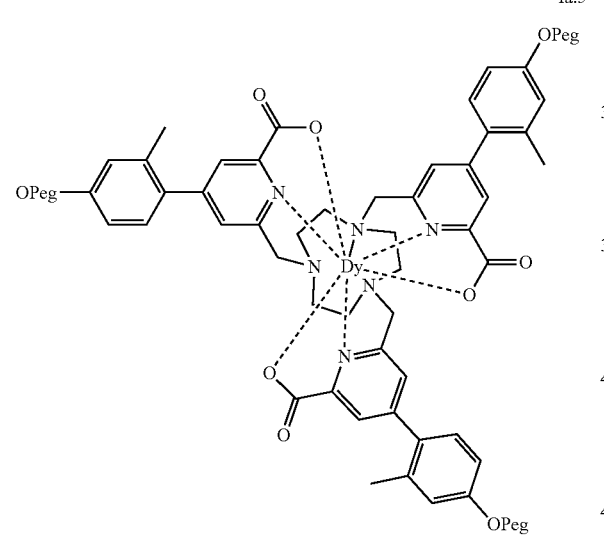

Ia.5

The ligand 6b (50 mg, 0.038 mmol) is solubilized in MeOH (5 mL) then 1 M NaOH (2 mL) is added and the solution is left under stirring at room temperature for 1 h. Then the pH is adjusted to pH 3~4 with 1 M HCl, then to pH ~7 with $Na_2CO_{3sat}$. $Dy(NO_3)_3 \cdot 5H_2O$ (20 mg, 0.056 mmol) is added and the solution is left at room temperature overnight. After concentration under reduced pressure, the mixture is purified by extractions/washes with $DCM/H_2$, and the organic phase evaporated to give the product in the form of a pale yellow solid (50 mg, 92%). HRMS (ESI) calculated for $C_{69}H_{87}DyN_6Na_2O_{18}$ 748.7577. Exp 748.7576 $[M+2Na]^{2+}$.

Complex Ia.6

Ia.6

6d (9 mg, 0.007 mmol) is dissolved in tetrahydrofuran (2 mL) and 1 M NaOH (2 mL) is added to pH 14. The reaction mixture is stirred at room temperature for 24 h. The pH of the solution is then adjusted to pH 6 with 1 M HCl then $DyCl_3 \cdot 6H_2O$ (3.2 mg, 0.008 mmol) is added and the solution is left under stirring at room temperature for 3 days. THF is then evaporated and a $CH_2Cl_2/H_2O$ extraction is carried out. The organic phases are combined and evaporated to obtain the pure dysprosium(III) complex (8 mg, 77%). HRMS (ESI) calculated for $C_{72}H_{93}N_6O_{18}DyNa_2$ 769.7811. Exp 769.7818 $[M+2Na]^{2+}$, $C_{72}H_{93}N_6O_{18}DyNa_3$ 520.8505. Exp 520.8521 $[M+3Na]^{3+}$; $t_R$=9.57 min (method HPLC-ESI-ACN-365, $H_2O/CH_3CN$ 85/15 to 0/100 in 16 min).

B. Evaluation of the Complexes

Example 3: Spectroscopic Properties

The properties of complexes Ia.1-Ia.6 and 8 were evaluated in methanol (Table 1) and water (Table 2). These properties were compared to those of complex 9, described in the document, *Dalton Trans*. 2015, 44, 4918, and of the following structure:

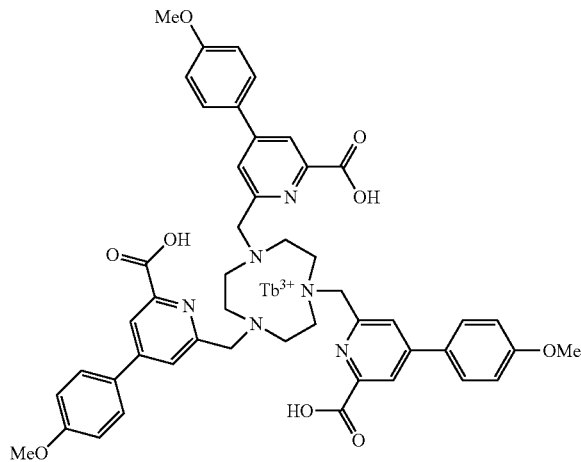

Photophysical measurements of the complexes show that terbium complexes Ia.1-Id.4 according to the invention have an intense absorption in methanol (Table 1).

Moreover, these complexes have very high quantum yields, and much higher than that of the complex 9 outside the invention, which has no substituent other than alpha hydrogen of the pyridine-phenyl bond (positions R2 and R3). The strong limitation, or even suppression, of internal rotation around the pyridine-phenyl bond thus significantly improves quantum efficiency.

The brightness of the complexes according to the invention is then higher than that of complex 9.

Different electron-donating groups were tested: methoxy, PEG or amide. Poorer results were observed with an amide group (complex Ia.3), due to a lower quantum yield, but still satisfactory in terms of brightness.

On the other hand, the presence of a second methoxy-type electron donor group on the phenyl group (complex 8) causes a drop in quantum efficiency, compared to a methyl group (complex Ia.1).

The introduction of a second methyl group has a major effect on the molar extinction coefficient with a decrease of more than 50%. Thus, despite excellent quantum efficiency, Ia.4 has a brightness at 330 nm lower than its counterpart Ia.2.

The spectroscopic properties of complexes Ia.2 and Ia.4 are stored in water (Table 2).

The brightness of complex Ia.2 is very high, and comparable to that of complex TbLumi-4, resulting from the work of the group of K. Raymond (J. Xu et al. *J. Am. Chem. Soc.* 2011, 133, 19900-19910), which is among the best complexes currently on the market ($\Phi$=59%, $\varepsilon$ of the order of 25000 L·mol$^{-1}$·cm$^{-1}$ and a brightness around 15000 L·mol$^{-1}$·cm$^{-1}$).

FIG. 1 shows the absorption and emission spectrum of complex Ia. 4 in water at room temperature.

TABLE 1

Photophysical properties of complexes Ia.1-Ia.6, 8 and 9 measured in methanol

| complex | λ max (nm) | ε (L·mol$^{-1}$·cm$^{-1}$) | Φ (%) | T (ms) | B at λ max (L·mol$^{-1}$·cm$^{-1}$) | B at 330 nm (L·mol$^{-1}$·cm$^{-1}$) |
|---|---|---|---|---|---|---|
| Ia.1 | 306 | 21000 | 74 | 1.33 | 15500 | n.d. |
| Ia.2 | 305 | 34800 | 74 | 1.32 | 26000 | 10000 |
| Ia.3 | 305 | 34800 | 35 | 0.79 | 12000 | 5600 |
| Ia.4 | 274 | 19000 | 65 | 1.59 | 12000 | 3400 |
|  | 302 | 13000 |  |  | 8500 |  |
| 8 (outside invention) | 325 | 51000 | 13 | 0.22 | 6600 | 6500 |
| Ia.5 | 306 | n.d. | 2.8 | 0.021 | n.d. | n.d. |
| Ia.6 | 301 | n.d. | 2.6 | 0.020 | n.d. | n.d. |
| 9 (outside invention) | 308 | 33000 | 12 | n.d. | 3900 | n.d. |

TABLE 2

Photophysical properties of complexes Ia.2 and Ia.4-Ia. 6 measured in water

| complex | λ max (nm) | ε (L·mol$^{-1}$·cm$^{-1}$) | Φ (%) | T (ms) | B at λ max (L·mol$^{-1}$·cm$^{-1}$) | B at 330 nm (L·mol$^{-1}$·cm$^{-1}$) |
|---|---|---|---|---|---|---|
| Ia.2 | 302 | 30400 | 74 | 1.36 | 23000 | 8900 |
| Ia.4 | 275 | 21000 | 66 | 1.46 | 14000 | 2500 |
|  | 300 | 11800 |  |  | 7800 |  |
| Ia.5 | 302 | n.d. | 1.8 | 0.017 | n.d. | n.d. |
| Ia.6 | 300 | n.d. | 2.5 | 0.028 | n.d. | n.d. |

Dysprosium complexes Ia.5 and Ia.6 also have remarkable photophysical properties in methanol and water. These complexes are among the most brilliant complexes reported in the literature.

Figure 2:
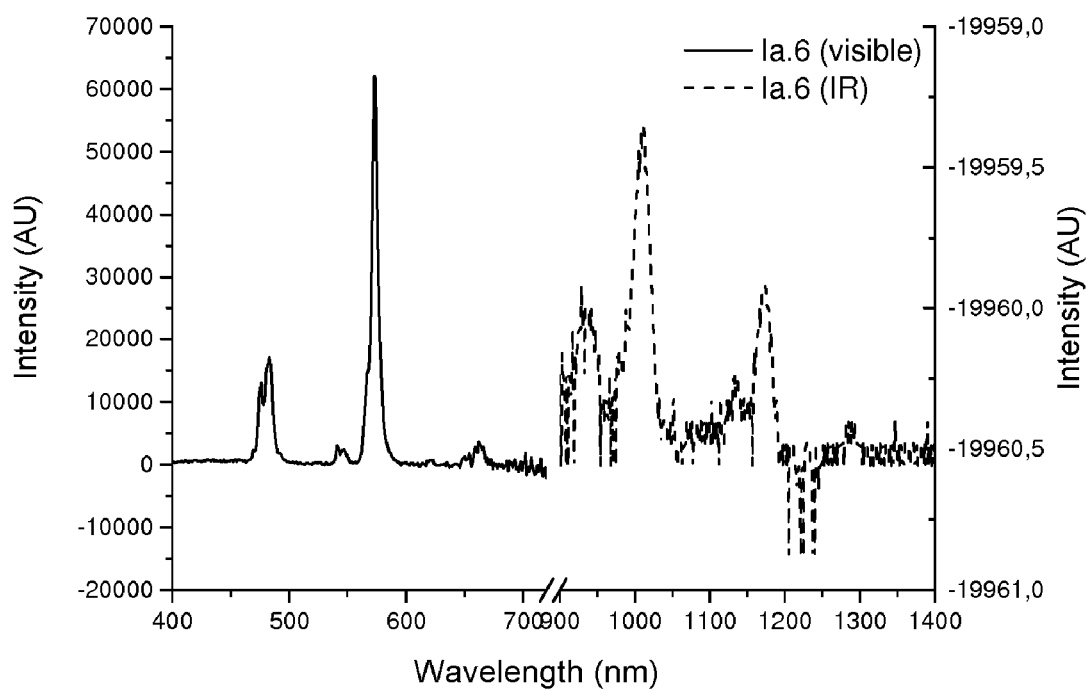
FIG. 2 shows the emission spectrum of complex Ia.6 in a 4:1 methanol/ethanol mixture at room temperature.

FIG. 2 shows the absorption and emission spectrum of complex Ia.6 in a methanol/ethanol mixture at room temperature.

Example 4: Cellular Imaging

Figure 3:
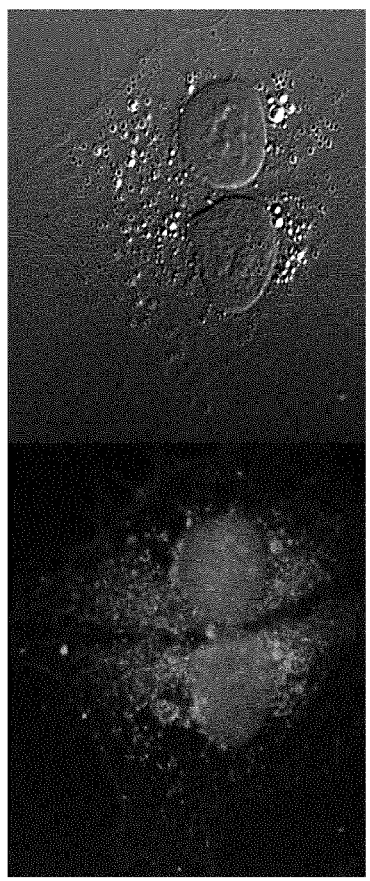
FIG. 3 shows images of cells attached to the PFA and labelled with the complex Ia.2 (biphotonic excitation $\lambda_{ex}$=720 nm), obtained with the visible emission of complex Ia.2 (left image) or obtained with DIC transmitted light (right image).

Complex Ia.2 has shown significant interest in single- or two-photon fluorescence microscopy imaging. FIG. 3 shows images of cells attached to the PFA and labelled with complex Ia.2 (concentration=$10^{-5}$ mol·L$^{-1}$, biphotonic excitation, $\lambda_{ex}$=720 nm), which clearly shows its internalization in the cell. The emission spectra confirm the presence of Ia.2 inside the cell and not in the buffer.

Figure 4:
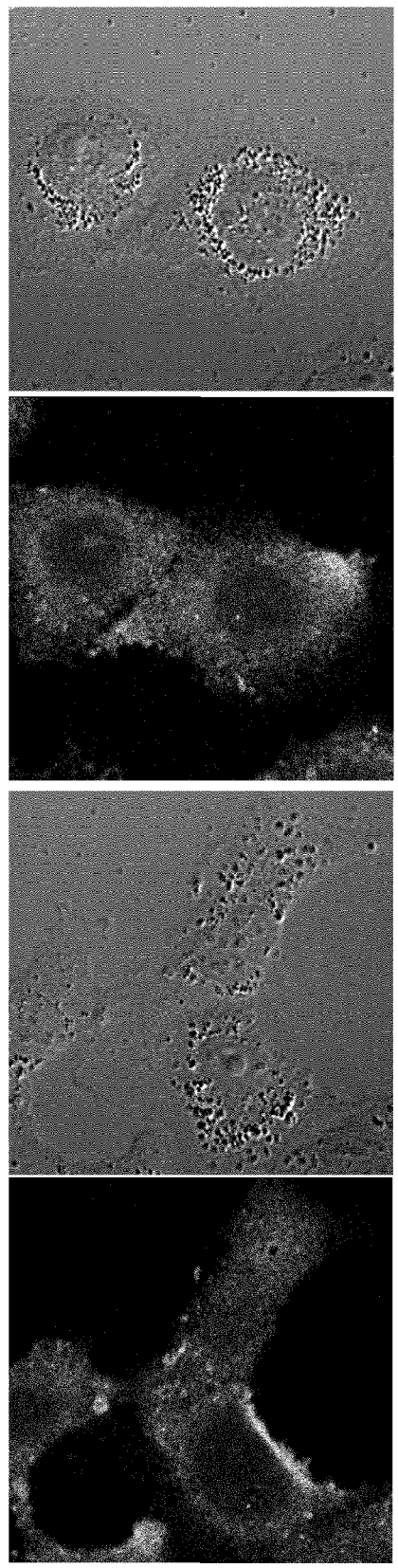
FIG. 4 shows images of cells fixed to the PFA and labelled with the complex Ia.5 (biphotonic excitation $\lambda_{ex}$=720 nm), obtained with the visible emission of the complex Ia.5 (images a and c) or obtained with DIC transmitted light (images b and d).

FIG. 4 shows images of T24 cells attached to the PFA and labelled with complex Ia.5 (concentration=$10^{-5}$ mol·L$^{-1}$, biphotonic excitation, $\lambda_{ex}$=720 nm). As with complex Ia.2, the internalization of complex Ia.5 in the cell is confirmed by the emission spectra.

The invention claimed is:

1. A lanthanide complex comprising a chelating agent, formed of a macrocycle or a ligand, complexing a lanthanide ion Ln$^{3+}$, wherein the lanthanide ion Ln$^{3+}$ is selected from terbium and dysprosium and in that the chelating agent includes at least a group (B) of the following structure:

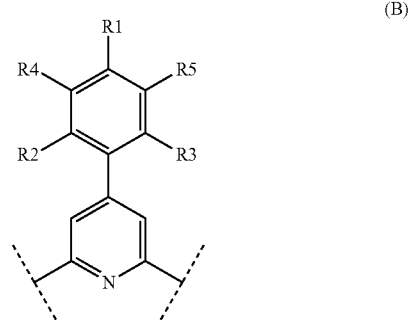

(B)

wherein:
—R1 represents a hydrogen, a group —R6, or an electron-donating group -E1,
—R2 represents a hydrogen, a group —R7, or an electron-donating group -E2,
—R3 represents a hydrogen, a group —R8, or an electron-donating group -E3,
—R4 and —R5, identical or different, independently represent a hydrogen or a group —R9 or —OR9,
-E1, -E2 and -E3 are independently selected from the groups consisting of —OR10, —SR10, —NH(CO)R10, —NH(CO)NR10R'10, —NH(CS)NR10 R'10 and —NH(CS)NHR10,
—R6, —R7, —R8, —R9, —R10 and R'10 identical or different, independently represent a (C1-C6) alkyl group, optionally substituted by a group —X1 or a group —Y,
—X1 is a reactive group,
—Y is a water-solubilizing group,
with the proviso that:
at least one of the substituents —R2 and —R3 is not hydrogen,
only one of the groups —R1, —R2 and —R3 represents an electron-donating group, and
said chelating agent comprises at most one reactive group.

2. The lanthanide complex according to claim 1 selected from the lanthanide complexes of formula (I):

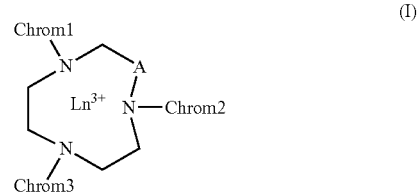

(I)

wherein:
Ln$^{3+}$ is a lanthanide selected from Tb and Dy,
-A- represents —CH$_2$— or —CH(L$_A$-X2)-,
-L$_A$- is a covalent bond, or a linear or branched (C1-C20) alkylene group, optionally containing one or more double or triple bonds, and optionally substituted by one to three groups —SO$_3$H, or -L$_A$- is a (C5-C8) cycloalkylene group or a (C6-C14) arylene group,
—X2 is a reactive group,
-Chrom1, -Chrom2 and -Chrom3 are identical or different and independently selected from the groups of formula (B1):

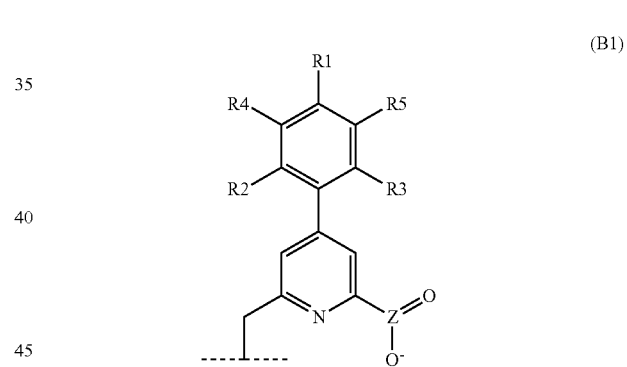

(B1)

—R1, —R2, —R3, —R4, and —R5 are as defined in claim 1,
—Z— represents —C— or —P(R$_Z$)—, and
—R$_Z$ represents a phenyl, benzyl, methyl, ethyl, propyl, n-butyl, sec-butyl, iso-butyl or tert-butyl group,
with the proviso that if -A- is —CH(L$_A$-X2)-, then none of groups -Chrom1, -Chrom2 and -Chrom3 of formula (B1) has group —X1.

3. The lanthanide complex according to claim 2, wherein -A- represents —CH$_2$— and —Z— represents —C—.

4. The lanthanide complex according to claim 2, wherein -Chrom1, -Chrom2 and -Chrom3 are identical, wherein:
—R1 represents an electron-donating group -E1 as defined in claim 1,
—R2 is a group —R7 as defined in claim 1, and
—R3 is a group —R8 as defined in claim 1.

5. The lanthanide complex according to claim 2 wherein:
-A- represents —CH$_2$—, -Chrom1 and -Chrom2 are identical and are of structure (B2):

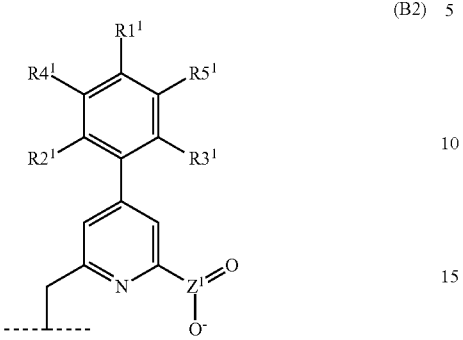

with —R1¹, —R2¹, —R3¹, —R4¹, —R5¹ and —Z¹— as defined respectively for R1, —R2, —R3, —R4, —R5 and —Z— in claim 1, with the proviso that Chrom1 and -Chrom2 do not have a reactive group, and -Chrom3 is different from -Chrom1 and from -Chrom2 and is of structure (B3):

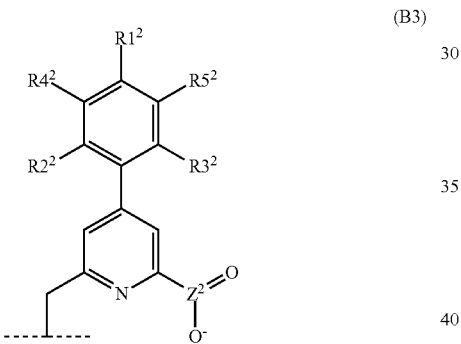

with —R1², —R2², —R3², —R4², —R5² and —Z²— as defined respectively for —R1, —R2, —R3, —R4, —R5 and —Z— in claim 1, with the proviso that -Chrom3 has a reactive group.

6. The lanthanide complex according to claim 1 selected from the lanthanide complexes of formula (II):

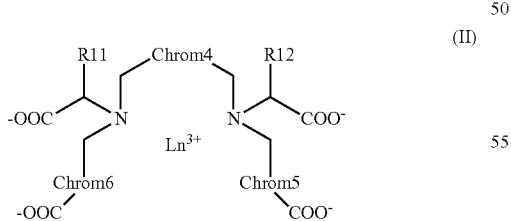

wherein:
Ln³⁺ is a lanthanide selected from Tb and Dy,
—R11 and —R12, identical or different, are independently selected from —X1, —Y, a hydrogen atom or a (C1-C6) alkyl group, and
-Chrom4-, -Chrom5-, and -Chrom6-, identical or different, independently represent a group of formula (B), as defined in claim 1.

7. The lanthanide complex according to claim 6, wherein -Chrom4-, -Chrom5- and -Chrom6- are identical, wherein:
—R1 represents an electron-donating group -E1 as defined in claim 1,
—R2 is a group —R7 as defined in claim 1, and
—R3 is a group —R8 as defined in claim 1.

8. The lanthanide complex according to claim 6, wherein:
either:
Chrom5- and -Chrom6- are identical and are of structure (B10):

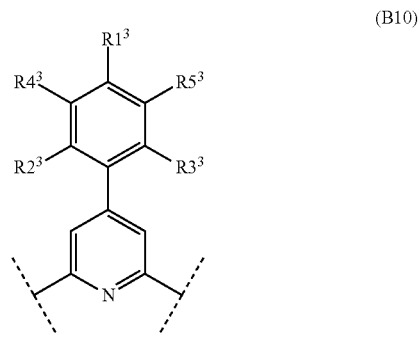

wherein —R1³, —R2³, —R3³, —R4³, and —R5³ are as defined respectively for —R1, —R2, —R3, —R4, and —R5 in claim 1, with the proviso that -Chrom5- and -Chrom6- do not have a reactive group, and Chrom4- is different from -Chrom5- and from -Chrom6- and is of structure (B11):

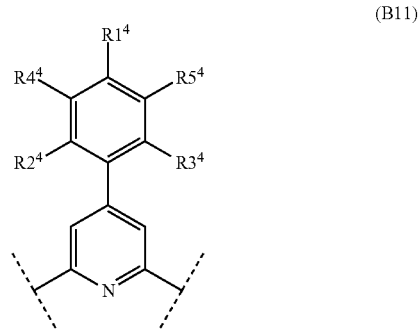

wherein —R1⁴, —R2⁴, —R3⁴, —R4⁴ and —R5⁴ are as defined respectively for —R1, —R2, —R3, —R4 and —R5 in claim 6, with the proviso that -Chrom4- has a reactive group —X1,
or:
-Chrom4- and -Chrom6- are identical and are of structure (B12):

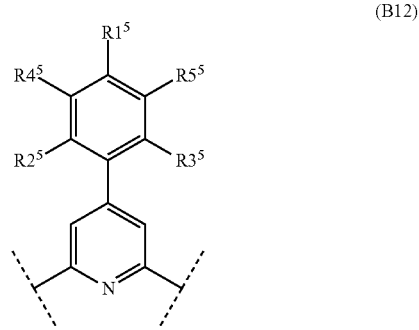

wherein —R1⁵, —R2⁵, —R3⁵, —R4⁵ and —R5⁵ are as defined respectively for —R1, —R2, —R3, —R4 and —R5 in claim 1, with the proviso that -Chrom4- and -Chrom6- do not have a reactive group, and -Chrom5- is different from -Chrom4- and from -Chrom6- and is of structure (B13):

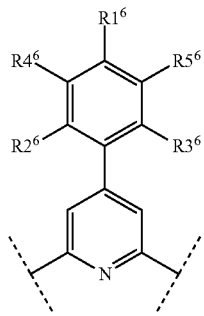

wherein —R1⁶, —R2⁶, —R3⁶, —R4⁶ and —R5⁶ are as defined respectively for —R1, —R2, —R3, —R4 and —R5 in claim 1, with the proviso that -Chrom5- has a reactive group —X1.

9. The lanthanide complex according to claim 1, wherein —R4 and —R5 represent hydrogens.

10. The lanthanide complex according to claim 1, comprising a single reactive group allowing its coupling by covalent bonding to a biomolecule

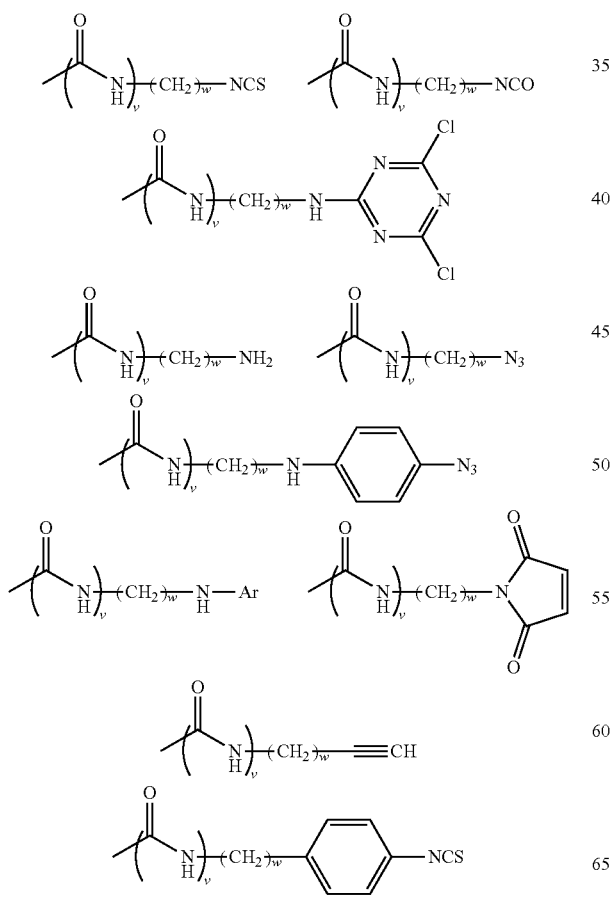

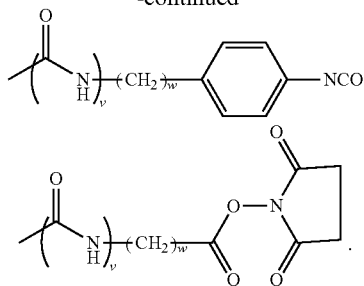

11. The lanthanide complex according to claim 1, wherein the group Y is selected from the group consisting of —SO₃⁻, —COO⁻, sulfobetaine and —O—[(CH₂)₂—O]ₘ—CH₃, m being an integer ranging from 1 to 10.

12. The lanthanide complex according to claim 1, wherein Ln³⁺ is terbium.

13. A chelating agent of formula (III):

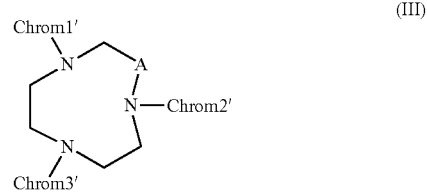

with -Chrom1'-, -Chrom2'-, and -Chrom3'-, identical or different, and independently selected from the groups of formula (B5):

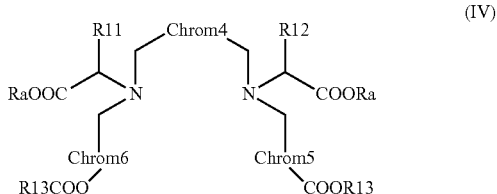

with R1, R2, R3, R4 and R5 as defined in claim 1, and —R13 an acid-protecting group, or in the form of a salt.

14. A chelating agent of formula (IV):

(IV)

RaOOC—CH(R11)—N(CH₂-Chrom4)—CH₂—CH₂—N(CH₂-Chrom5)—CH(R12)—COORa
                    |                                    |
                    Chrom6                               Chrom5
                    R13COO                               COOR13 with -Chrom4-, -Chrom5- and -Chrom6- as defined in claim 6, and —R13 an acid-protecting group, or in the form of a salt.

15. A method for detecting a biomolecule comprising the steps of
coupling a luminescent complex according to claim 1, comprising a reactive group with said biomolecule on the reactive group of said luminescent complex, and detecting the luminescence of a conjugate of said biomolecule with said luminescent complex.

16. The lanthanide complex according to claim 2, wherein —RZ represents a phenyl or a methyl group.

17. The lanthanide complex according to claim 4, wherein:
—R1 represents an electron-donating group -E1 selected from the groups consisting of —OR10 and —NH(CO)R10, —R10 being as defined in claim 1,
—R2 is -Me, and
—R3 is -Me or a hydrogen.

18. The lanthanide complex according to claim 4, wherein —R1 represents —OMe or —OPEG.

19. The lanthanide complex according to claim 5, wherein:
—$R1^1$ is a group —O(C1-C6) alkyl substituted by a group —Y,
—$R1^2$ is a group —O(C1-C6) alkyl substituted by a group —X1,
—$R2^1$ and —$R2^2$, identical or different, represent a group —R7 as defined in claim 1, and
—$R3^1$, —$R3^2$, —$R4^1$, —$R4^2$, —$R5^1$, and —$R5^2$ are hydrogens.

20. The lanthanide complex according to claim 5, wherein —$R2^1$ and —$R2^2$ are identical.

21. The lanthanide complex according to claim 5, wherein —$R2^1$ and —$R2^2$ represent a (C1-C6) alkyl group.

22. The lanthanide complex according to claim 10, wherein the reactive group is selected from the group consisting of —COOH, —$NH_2$, an acrylamide, an activated amine, an activated ester, an aldehyde, an alkyl halide, an anhydride, an aniline, an azide, an aziridine, a carboxylic acid, a diazoalkane, a haloacetamide, a halotriazine, a hydrazine, an imido ester, an isocyanate, an isothiocyanate, a maleimide, a sulfonyl halide, a thiol, a ketone, an acid halide, a hydroxysuccinimidyl ester, a succinimidyl ester, a hydroxysulfosuccinimidyl ester, an azidonitrophenyl, an azidophenyl, a 3-(2-pyridyl dithio)-propionamide, a glyoxal, a triazine, and an acetylenic group, and the groups of formula:

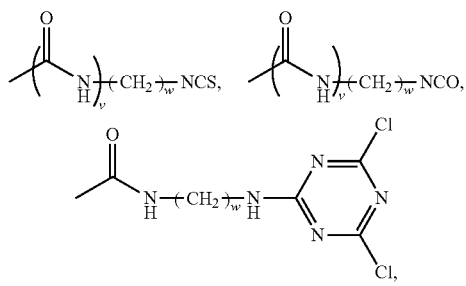

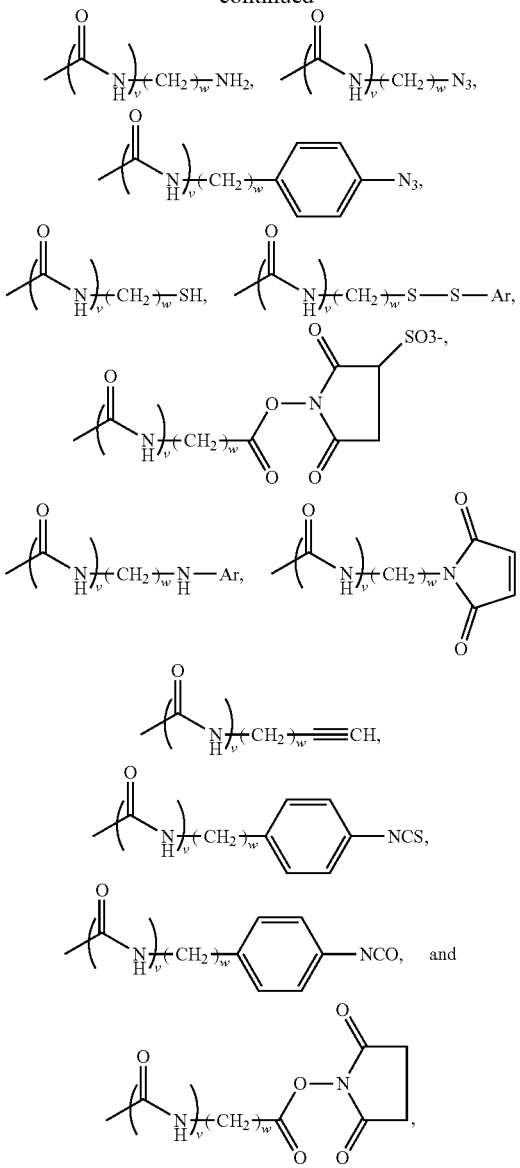

wherein w is an integer belonging to the range from 0 to 8 and v is equal to 0 or 1, and Ar is a saturated or unsaturated 5- or 6-membered heterocycle, comprising 1 to 3 heteroatoms, optionally substituted by a halogen atom.

23. The lanthanide complex according to claim 10, wherein the reactive group is selected from —COOH, —$NH_2$, succinimidyl esters, haloacetamides, azides, hydrazines, isocyanates and maleimides.

* * * * *